(12) United States Patent
Hallen

(10) Patent No.: US 12,175,630 B2
(45) Date of Patent: Dec. 24, 2024

(54) DIGITAL IMAGE OPTIMIZATION FOR OPHTHALMIC SURGERY

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 432 days.

(21) Appl. No.: 17/376,694

(22) Filed: Jul. 15, 2021

(65) Prior Publication Data

US 2022/0020118 A1    Jan. 20, 2022

Related U.S. Application Data

(60) Provisional application No. 63/052,373, filed on Jul. 15, 2020.

(51) Int. Cl.
| | |
|---|---|
| *G06T 5/00* | (2024.01) |
| *A61B 1/313* | (2006.01) |
| *A61B 5/00* | (2006.01) |
| *G06T 3/4046* | (2024.01) |
| *G06T 3/4053* | (2024.01) |

(52) U.S. Cl.
CPC ............ *G06T 5/00* (2013.01); *A61B 1/313* (2013.01); *A61B 5/7203* (2013.01); *A61B 5/7267* (2013.01); *G06T 3/4046* (2013.01); *G06T 3/4053* (2013.01); *G06T 2207/10068* (2013.01); *G06T 2207/20081* (2013.01); *G06T 2207/20084* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 9,560,959 B1 * | 2/2017 | Hopkins | A61B 3/13 |
| 9,849,034 B2 * | 12/2017 | Artsyukhovich | A61B 3/1233 |
| 2014/0163389 A1 * | 6/2014 | Kudenov | A61B 5/0071 600/476 |
| 2017/0135568 A1 * | 5/2017 | Charles | G06T 7/38 |
| 2018/0144447 A1 | 5/2018 | Tate et al. | |
| 2019/0297276 A1 * | 9/2019 | Sachdev | G16H 30/40 |
| 2020/0035362 A1 | 1/2020 | Abou Shousha et al. | |
| 2021/0104313 A1 | 4/2021 | Mizobe et al. | |
| 2021/0224997 A1 | 7/2021 | Kushida et al. | |

FOREIGN PATENT DOCUMENTS

| | | |
|---|---|---|
| JP | 2018005841 A | 1/2018 |
| WO | 2019240257 A1 | 12/2019 |
| WO | WO-2020205655 A1 * | 10/2020 .......... B60W 30/182 |

* cited by examiner

*Primary Examiner* — Jiangeng Sun

(57) ABSTRACT

The present disclosure provides a digital image optimization system including a camera that includes at least one sensor that detects light reflected off an eye and sends a signal corresponding to the detected light to a processor. The system further includes an image processing system including the processor and that executes instructions to produce a digital image of the eye. The image processing system also executes instructions to apply a digital image optimization algorithm including a trained machine-learning model to the digital image of the eye to generate an optimized digital image of the eye. The system further includes a digital display that displays the optimized digital image of the eye.

13 Claims, 15 Drawing Sheets

DIGITAL IMAGE OPTIMIZATION FOR OPHTHALMIC SURGERY

TECHNICAL FIELD

The present disclosure relates to ophthalmic surgery and surgical equipment, and more specifically, to a digital image optimization system to improve digital visualization for ophthalmic surgery and associated methods.

BACKGROUND

Ophthalmic surgery is surgery performed on the eye or any part of the eye. Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

One type of ophthalmic surgery, vitreoretinal surgery, encompasses various delicate procedures involving internal portions of the eye, such as the vitreous humor, the retina, and the vitreoretinal membrane. Different vitreoretinal surgical procedures are used, sometimes with lasers, to improve visual sensory performance in the treatment of many eye diseases, including epimacular membrane, diabetic retinopathy, vitreous hemorrhage, macular hole, detached retina, and complications of cataract surgery, among others.

During ophthalmic surgery, such as vitreoretinal surgery, an ophthalmologist typically uses a non-electronic, optical, surgical microscope with oculars to view a magnified image of the eye undergoing surgery. More recently, vitreoretinal surgeons may use an ocular-free digital image system to aid visualization during vitreoretinal surgery. These systems may include a three-dimensional (3D) high dynamic range ("HDR") camera system with a pair of two-dimensional (2D) complementary metal-oxide-semiconductor (CMOS) single chip or three-chip sensors that allows the surgeon to view the retina on a display screen using polarized glasses, digital oculars or a head-mounted display. The display screen provides relief from having to view the surgery using oculars and allows others in the operating room to see exactly as the surgeon does. The system also allows for improved digital images under high magnification, and increased depth of field compared to a conventional optical, analog surgical microscope, which allow for improved visualization of the eye.

SUMMARY

The present disclosure provides a digital image optimization system to improve digital visualization for ophthalmic surgery and associated methods. The digital image optimization system includes a camera including at least one sensor that detects light reflected off an eye and sends a signal corresponding to the detected light to a processor. The digital image optimization system also includes an image processing system including the processor. The image processing system executes instructions to produce a digital image of the eye and executes instructions to apply a digital image optimization algorithm including a trained machine-learning model to the digital image of the eye to generate an optimized digital image of the eye. The digital image optimization system also includes a digital display that displays the optimized digital image of the eye.

The digital image optimization system and its methods of use may include the following additional features: i) the digital image optimization algorithm may at least partially reduce instrument glare, optical aberration, vitreous fog, or any combination thereof, in the digital image of the eye to generate the optimized digital image of the eye; ii) the optimized digital image of the eye may have contrast, sharpness, clarity, dynamic range, or any combination thereof that is the same or increased than that of the digital image of the eye; iii) the optimized digital image of the eye may have noise, distortion, vignetting, or any combination thereof that is the same or decreased than that of the digital image of the eye; iv) the digital image optimization algorithm may utilize interpolation, multi-exposure image noise reduction, or a combination thereof to generate the optimized digital image of the eye; v) the trained machine-learning model may have been trained using a plurality of training images from a red boost library; vi) the trained machine-learning model may have been trained using a plurality of digital images of the eye captured at a beginning of a surgery and a plurality of corresponding digital images of the eye captured at a conclusion of the surgery; vii) the digital image optimization system may be a component of an NGENUITY® 3D Visualization System (Novartis AG Corp., Switzerland).

The present disclosure further provides a digital image optimization system that includes a camera including at least one sensor that detects light reflected off a fellow eye and sends a signal corresponding to the detected light to a processor. The at least one sensor also detects light reflected off an operative eye and sends a signal corresponding to the detected light to the processor. The digital image optimization system also includes an image processing system including the processor. The image processing system executes instructions to produce a template digital image of the fellow eye, executes instructions to produce a digital mirror image of the template digital image, executes instructions to produce a working digital image of the operative eye, and executes instructions to align the digital mirror image to the working digital image to generate a retina arcade alignment template. The digital image optimization system also includes a digital display that displays the working digital image and the retina arcade alignment template.

The digital image optimization system and its methods of use may include the following additional features: i) the retina arcade alignment template may be displayed as an overlay to the working digital image; ii) the template digital image may include an eye structure that is a retina of the fellow eye, a central retina vein of the fellow eye, a retina arcade of the fellow eye, an optic disk of the fellow eye, or any combination thereof; iii) the working digital image may include an eye structure that is a retina of the operative eye, a central retina vein of the operative eye, a retina arcade of the operative eye, an optic disk of the operative eye, or any combination thereof; iv) the working digital image may include an equivalent field of view of the operative eye to a field of view of the template digital image of the fellow eye; v) aligning the digital mirror image to the working digital image may include aligning eye structures that are an optic disk of the fellow eye and an optic disk of the operative eye, a central retina vein of the fellow eye and a central retina vein of the operative eye, arterial vein crossings of the fellow eye and arterial vein crossings of the operative eye, branch veins of the fellow eye and branch veins of the operative eye, or any combination thereof; vi) the digital image optimization system may be a component of an NGENUITY® 3D Visualization System (Novartis AG Corp., Switzerland).

The present disclosure further provides a digital image optimization system that includes an endoscope including an optical fiber. The digital image optimization system also includes a camera including at least one sensor that detects light reflected off an interior of an eye and propagated through the optical fiber. The sensor sends a signal corresponding to the detected light to a processor. The digital image optimization system also includes an image processing system including the processor. The image processing system executes instructions to produce an endoscope digital image of the eye, and executes instructions to apply an endoscope digital image optimization algorithm that includes a trained machine-learning model to the endoscope digital image of the eye to generate an optimized endoscope digital image of the eye. The digital image optimization system also includes a digital display that displays the optimized endoscope digital image of the eye.

The digital image optimization system and its methods of use may include the following additional features: i) the endoscope digital image optimization algorithm may utilize interpolation, multi-exposure image noise reduction, or a combination thereof, to generate an optimized endoscope digital image of the eye; ii) the machine-learning model may have been trained using a plurality of training images including a plurality of endoscope digital images of the eye that were successfully optimized using an image processing method; iii) the endoscope digital image optimization algorithm may utilize single image super resolution to generate the optimized endoscope digital image of the eye; iv) the single image super resolution may use a very-deep super-resolution neural network; v) the endoscope digital image optimization algorithm may at least partially reduce noise, increase resolution, improve digital image quality, or any combination thereof, of the endoscope digital image of the eye; vi) the digital image optimization system may be a component of an NGENUITY® 3D Visualization System (Novartis AG Corp., Switzerland).

The present disclosure further provides an optimization network that includes a digital image optimization system. The digital image optimization system includes a camera including at least one sensor that detects light reflected off an eye and sends a signal corresponding to the detected light to a first processor. The digital image optimization system further includes a first image processing system that includes the first processor and executes instructions to produce a digital image of the eye. The digital image optimization system further includes a digital display. The optimization network also includes a communication network communicatively coupled to the digital image optimization system and a digital image management system. The optimization network sends the digital image of the eye to the digital image management system. The optimization network also includes the digital image management system. The digital image management system includes a second image processing system including a second processor and a trained machine learning model. The second image processing system executes instructions to process the digital image of the eye using the trained machine learning model to calculate an optimized digital image of the eye and sends the optimized digital image of the eye to the digital display. The digital display displays the optimized digital image of the eye.

The optimization network and its methods of use may include the following additional features: i) the second image processing system may be stored locally as part of the first image processing system; ii) the second image processing system may operate on a server; iii) the second image processing system may provide cloud-based digital image optimization services; iv) the trained machine learning model may have been trained using a plurality of training images; v) the plurality of training images may include a plurality of digital images of the eye captured at the beginning of a surgery and a plurality of paired digital images of the same eye captured at a conclusion of the surgery; vi) the plurality of training images may include a plurality of endoscope digital images of the eye that were successfully optimized using an image processing method; the plurality of training images may have been captured using an NGENUITY® 3D Visualization System (Novartis AG Corp., Switzerland); vii) the plurality of training images may be uploaded to the digital image management system using the communication network; viii) the trained machine learning model may have been trained using an integrated architecture including a convolutional neural network and at least one long term short-term memory unit; ix) the digital image optimization system may a component of an NGENUITY® 3D Visualization System (Novartis AG Corp., Switzerland).

The present disclosure further provides a digital time out system that includes an identity marker affixed to a patient that includes machine readable information. The digital time out system also includes a camera including at least one sensor that acquires the machine-readable information and sends a signal corresponding to the machine-readable information to a processor. The digital time out system also includes an image processing system including the processor and that processes the machine-readable information to determine patient data. The image processing system also determines discrepancies, agreement, or a combination thereof between patient data and information provided to a surgeon, staff in the operating room, or a combination thereof.

The digital time out system and its methods of use may include the following additional features: i) the digital time out system may further include a digital display that displays discrepancies, agreement, or a combination thereof between patient data and information provided to a surgeon, staff in the operating room, or a combination thereof; ii) the identity marker may be affixed above an eye of the patient; iii) the identity marker may be a removable decal tattoo, a patch, a sticker, tape, or any combination thereof; iv) the identity marker may further include a locator; v) the machine-readable information may be a single dimension barcode, a multidimensional barcode, a Quick Response code, symbols, or any combination thereof; vi) the digital time out system may be a component of an NGENUITY® 3D Visualization System (Novartis AG Corp., Switzerland); vii) the patient data may include information associated with the patient that is identification information associated with the patient, medical information associated with the patient, indexing information, or any combination thereof; viii) the camera may detect light reflected off an eye and send a signal corresponding to the detected light to a first processor, and the image processing system may execute instructions to produce a digital image of the eye; ix) the system may include a communication network communicatively coupled to the digital time out system and a digital image management system. The communication network may send the digital image of the eye to the digital image management system. The digital image management system may include a second image processing system that includes a second processor and a trained machine-learning model. The machine-readable data may include indexing information that is associated with the digital image of the eye and is stored in the digital image management system; x) the trained machine-learning model may have been trained using a plurality of training images that include the digital image of the eye. The plurality of training images may have been selected based on the indexing information associated with the digital image of the eye.

The present disclosure further provides a method of optimizing a digital image of an eye by capturing a digital image of an eye with a camera; applying a digital image optimization algorithm to generate an optimized digital image of the eye using an image processing system; and displaying the optimized digital image of the eye on a digital display. The digital image optimization algorithm may at least partially reduce instrument glare, optical aberration, vitreous fog, or any combination thereof, in the digital image of the eye to generate the optimized digital image of the eye. The digital image optimization algorithm may be a trained machine-learning model. The trained machine-learning model may have been trained using a plurality of digital images of the eye captured at a beginning of a surgery and a plurality of corresponding digital images of the eye captured at a conclusion of the surgery. The camera may be a component of an NGENUITY® 3D Visualization System (Novartis AG Corp., Switzerland).

The present disclosure further provides a method of generating a digital image optimization algorithm by capturing a plurality of input digital images of an eye at a beginning of a surgery; capturing a plurality of output digital images of the eye at a conclusion of the surgery; using the plurality of input digital images of the eye and the plurality of output digital images of the eye as training images to train a machine learning model; and using the trained machine-learning model as a digital image optimization algorithm.

The present disclosure further provides a method of optimizing a digital image of an eye by capturing a digital image of a fellow eye; capturing a digital image of an operative eye; generating a mirror image of the digital image of the fellow eye; aligning the mirror image of the digital image of the fellow eye to the digital image of the operative eye to generate a retina arcade alignment template; displaying the retina arcade alignment template as an overlay to the digital image of the operative eye on a digital display; and performing ophthalmic surgery on the operative eye using the retina arcade alignment template. The mirror image of the digital image of the fellow eye may be aligned to the digital image of the operative eye by aligning the optic disk, the central retina vein, arterial vein crossings, branch veins, or any combination thereof.

The present disclosure further provides a method of optimizing an endoscope digital image of an eye by capturing an endoscope digital image of an eye using an endoscope; applying an endoscope digital image optimization algorithm to generate an optimized endoscope digital image of the eye; and displaying the optimized endoscope digital image of the eye on a digital display. The endoscope digital image optimization algorithm may use interpolation, multi-exposure image noise reduction, machine learning, deep learning, or any combination thereof.

The present disclosure further provides a method of generating an endoscope digital image optimization algorithm by capturing a plurality of endoscope digital images of an eye; optimizing the plurality of endoscope digital images of the eye using an image processing method to generate a plurality of optimized endoscope digital images of the eye; using the plurality of endoscope digital images of the eye as input images and the plurality of optimized endoscope digital images of the eye as output images to train a machine-learning model; and using the trained machine-learning model as an endoscope digital image optimization algorithm.

The present disclosure further provides a method of training a machine-learning model by inputting a plurality of training images including a plurality of input images and a plurality of corresponding output images into an integrated architecture using an image processing system; using a convolutional neural network to generate feature representations for the plurality of input images; using the integrated architecture to calculate a plurality of hypothesis differentials between a plurality of predicted optimized digital images of an eye and the plurality of corresponding output images; calculating a loss between the plurality of hypothesis differentials and a plurality of differentials calculated between the plurality of input images and the plurality of corresponding output images; evaluating if an overall loss is smaller than a pre-defined threshold value; if the overall loss is not smaller than the pre-defined threshold value, updating parameters of the integrated architecture; and if the overall loss is smaller than the pre-defined threshold value, storing the parameters of the integrated architecture and ending training. The loss may be calculated using a loss function. The loss function may be a smooth L1 loss function. The plurality of hypothesis differentials may be calculated using the feature representations for the plurality of input images. The image processing system may operate on a server once the machine-learning model is trained. The image processing system may provide cloud-based digital image optimization services.

The present disclosure further provides a method of carrying out a digital time out by acquiring machine-readable information printed on an identity marker affixed to a patient using a camera; processing the machine-readable information using an image processing system; determining a correctness of an identity of the patient based on the machine-readable information; if the identity of the patient is incorrect, stopping a planned medical procedure; if the identity of the patient is correct, determining a correctness of the planned medical procedure based on the machine-readable information; if the planned medical procedure is incorrect, stopping the planned medical procedure; and if the planned medical procedure is correct, carrying out the planned medical procedure.

The present disclosure further provides a method of optimizing a digital image of an eye by capturing a digital image of an eye using a digital image optimization system; associating the digital image of the eye with processed machine-readable information; training a machine-learning model using the digital image of the eye; processing the digital image of the eye using a trained machine-learning model; generating an optimized digital image of the eye using an image processing system; and displaying the optimized digital image of the eye on a digital display. The digital image of the eye may be selected for inclusion in a set of training images based on the processed machine-readable information.

Aspects of the digital image optimization system and its methods of use may be combined with one another unless clearly mutually exclusive. In addition, the additional features of the digital image optimization system and its associated methods described above may also be combined with one another unless clearly mutually exclusive.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

Figure 1:
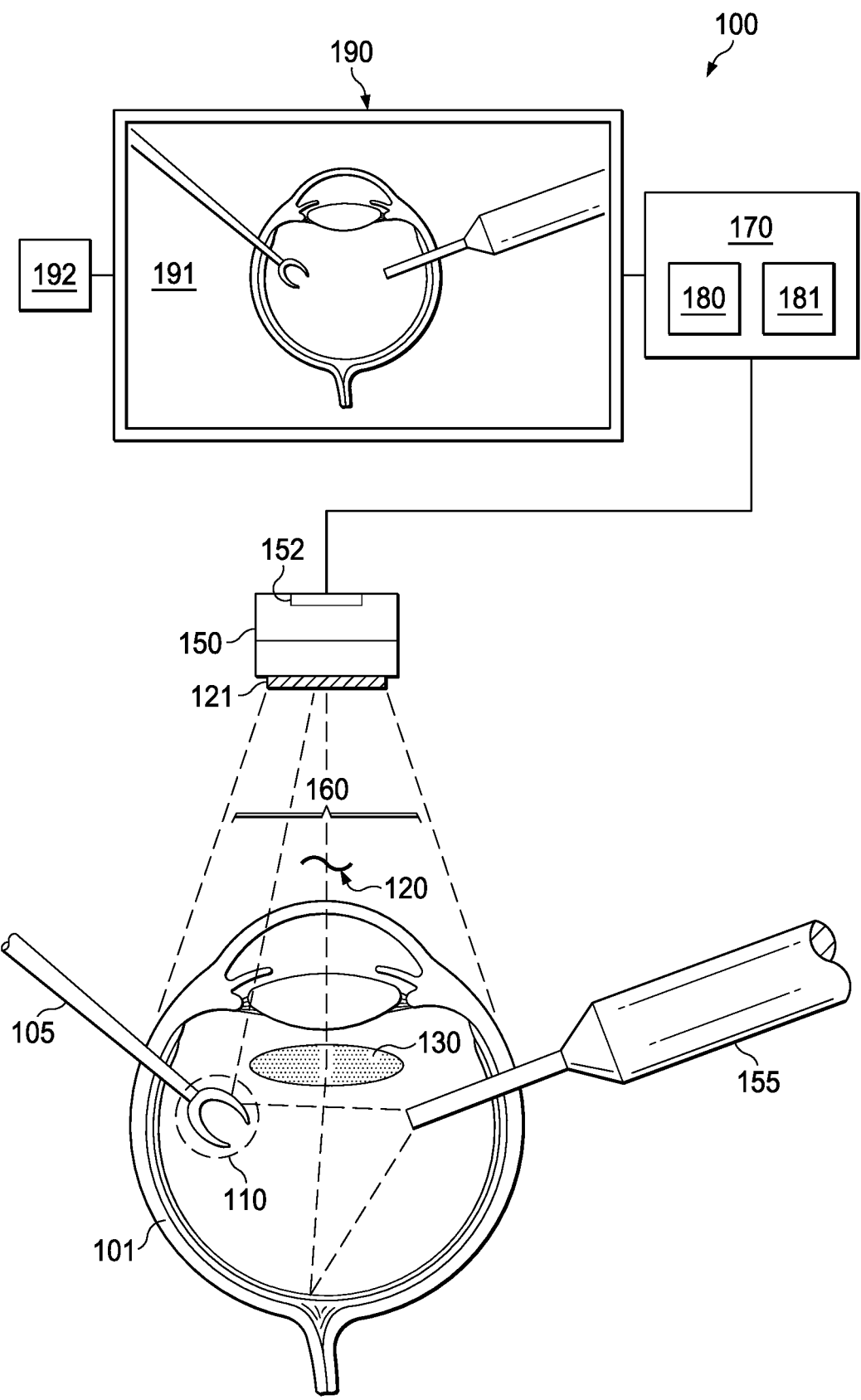
FIG. 1 is a schematic representation of a digital image optimization system including a camera, an image processing system, and a digital display.

The present disclosure provides systems including digital image optimization to improve digital visualization for ophthalmic surgery and associated methods.

Ophthalmic surgeons face unique challenges when visualizing the eye. In particular, aberrations during medical procedures may reduce the quality of a digital image of an eye. For example, any view obtained through the patient's pupil is subject to optical aberration, which may distort a digital image of the eye. Optical aberration may be caused by eye diseases or prior surgery causing corneal asphericity or intraocular lens implants which lead to an aberrated image viewed by the surgeon. Vitreous haze may also reduce digital image quality. In addition, stainless steel instruments inserted into the eye may produce glare that reduces the image quality when viewing the eye during surgery. In other examples, a low-resolution digital image, such as an endoscope digital image of about 30,000 pixels, may be displayed on a high-resolution digital display of over one million pixels. This may result in poor image quality of the endoscope digital image.

Poor image quality may interfere with the ability of the surgeon to visualize the interior of the eye and make surgery more difficult. In analog systems there are very limited ways to correct for the effect of aberrations, and many are simply uncorrectable. Digital visualization systems do allow for various corrective measures, which may improve a digital image of the eye presented to the surgeon and others assisting with ophthalmic surgery. However, current systems and methods may not make use of optimization algorithms, which may include machine-learning models, to improve the quality of the digital image of the eye. Furthermore, current systems and methods may not utilize identity markers to catalogue digital images of the eye for use in optimization algorithms. In such cases, the digital image of the eye may have reduced image quality. For example, the digital image of the eye may have reduced contrast, sharpness, clarity, and dynamic range, and may have increased noise, distortion, and vignetting. Reduced image quality may increase the risk of complications during ophthalmic surgery.

The digital image optimization systems and methods of the present disclosure may provide for faster, safer, and more efficient medical procedures by improving digital visualization for ophthalmic surgery. The digital image optimization systems and methods disclosed herein may improve digital visualization for ophthalmic surgery by providing an optimized digital image that has reduced instrument glare, reduced optical aberration, reduced vitreous haze, or any combination thereof, as compared to a digital image provided by other systems and methods. The digital image optimization systems and methods disclosed herein may improve digital visualization for ophthalmic surgery as compared to current systems and methods by providing a retina arcade alignment template for alignment of retina attachment during surgery. The digital image optimization systems and methods disclosed herein may improve digital visualization for ophthalmic surgery by providing an optimized digital image that is a super resolution digital image. The systems and methods of the present disclosure may improve digital visualization for ophthalmic surgery as compared to current systems and methods by including a machine-learning model to optimize a digital image of the eye. The digital image optimization systems and methods disclosed herein may improve digital visualization for ophthalmic surgery by providing training images to train the machine-learning model. The training images may be a plurality of digital images of a plurality of eyes from a plurality of medical procedures. The digital image optimization systems and methods disclosed herein may improve digital visualization for ophthalmic surgery by providing cloud-based digital image optimization services. The digital image optimization systems and methods disclosed herein may improve digital visualization for ophthalmic surgery by providing a digital time out. A digital time out may include a computational check that the medical information associated with a patient matches the information provided to a surgeon, staff in the operating room, or a combination thereof.

The systems and methods disclosed herein may improve digital visualization for ophthalmic surgery by providing a digital image optimization system that may improve the contrast, sharpness, clarity, and dynamic range of a digital image of the eye, and may decrease the noise, distortion, and vignetting of the digital image of the eye. The digital image optimization system may be a component of a Digitally Assisted Vitreoretinal Surgery ("DAVS") system, or may be a component of the NGENUITY® 3D Visualization System (Novartis AG Corp., Switzerland). For example, the digital image of the eye may be captured with a camera or an endoscope. The systems and methods disclosed herein may use a machine-learning model to optimize a digital image of the eye. The systems and methods disclosed herein may use a retina arcade alignment template to align digital images of the same eye captured at different stages during surgery and provide an optimized digital image for reattachment of a retina following a vitrectomy. The systems and methods disclosed herein may also provide an optimization network that may allow cloud-based digital image optimization services. The optimization network may be a component of a Digitally Assisted Vitreoretinal Surgery ("DAVS") system, or may be a component of the NGENUITY® 3D Visualization System (Novartis AG Corp., Switzerland). The systems and methods disclosed herein may also provide a digital time out system that includes machine-readable information about a digital image of the eye. The machine-readable information may be useful in record keeping for storing digital images of the eye in the optimization network and in selecting training images to train the machine-learning model. The digital time out system may be a component of a Digitally Assisted Vitreoretinal Surgery ("DAVS") system, or may be a component of the NGENUITY® 3D Visualization System (Novartis AG Corp., Switzerland).

Referring now to FIG. 1, a digital image optimization system 100 may include a camera 150, an image processing system 170, and a digital display 190. The image processing system 170 may provide an optimized digital image of an eye 101. The camera 150 may capture a digital image of the eye 101. The digital image of the eye 101 captured by the camera 150 may include a field of view 160. The field of view 160 may include a close-up view of the eye 101, and may include a higher magnification view of the macula, vitreous humor, or other areas of the eye 101. The field of view 160 may also include a surgical instrument 105. The surgical instrument 105 may be a cannula, or may be another surgical tool used in ophthalmic surgery.

The camera 150 may be a digital camera, an HDR camera, a 3D camera, or any combination thereof. The camera 150 may be a component of an NGENUITY® 3D Visualization System (Novartis AG Corp., Switzerland). The camera 150 may also be a camera coupled to a microscope. The camera 150 may replace the oculars on a microscope, and may be a fifth-generation image capture module (ICM5) 3D surgical camera. The camera 150 may be configured to provide a stereoscopic digital image of the eye 101 (not shown). The camera 150 may include a lens 121. The lens 121 may also be an opto-mechanical focus lens, a manual focus lens, or a combination thereof. The camera 150 may also include at least one image sensor 152, which may be a charge-coupled device (CCD) sensor or a complementary metal-oxide semiconductor (CMOS) sensor. The camera 150 may be a monochrome camera, or may be a color camera, and the at least one image sensor 152 may be a monochrome image sensor or may be a color image sensor. The at least one image sensor 152 may be an image sensor with a color filter array, for example a Bayer filter, or may be an image sensor without a color filter array.

The digital image optimization system 100 may include a visible light illumination source 155. The visible light illumination source 155 may be a visible light illumination source for the camera 150. The visible light illumination source 155 may be an endoilluminator. The visible light illumination source 155 may include a xenon source, a white LED light source, or any other suitable visible light source. The visible light illumination source 155 may illuminate interior structures of the eye 101.

Light emitted by the visible light illumination source 155 and reflected off the surgical instrument 105 may cause instrument glare 110. Instrument glare 110 may also be caused by light emitted by other illumination sources. Instrument glare 110 may appear as noise or distortion in a digital image of the eye 101 captured by the camera 150.

Light emitted by the visible light illumination source 155 and reflected off the interior of the eye 101 may also be affected by optical aberration 120. Optical aberration 120 may be caused by a cloudy cornea, which may be caused by a long medical procedure or an eye defect, a cloudy lens, which may be caused by a cataract, or blood in the eye. Optical aberration 120 may also be caused by other features of the eye 101, the surgical setup, or a combination thereof. Optical aberration 120 may reduce the contrast, sharpness, clarity, and dynamic range of a digital image of the eye 101 captured by the camera 150.

Light emitted by the visible light illumination source 155 and reflected off the eye 101 may be subject to vitreous haze 130, which, for example, may appear as haze or fog in a digital image of the eye 101 captured by the camera 150.

A digital image captured by the camera 150 may be processed by the image processing system 170. The image processing system 170 may include a processor 180. The camera 150 may detect light reflected off the interior of the eye 101 into the lens 121 using the at least one image sensor 152, which may send a signal corresponding to the detected light to the processor 180. The processor 180 may execute instructions to produce a digital image of the eye 101. The image processing system 170 may also include a memory medium 181. The digital image of the eye 101 may be stored in the memory medium 181.

The processor 180 may execute instructions to apply a digital image optimization algorithm to the digital image of the eye 101 to produce an optimized digital image of the eye 191. The digital image optimization algorithm may be an algorithm that is a trained machine-learning model. A machine-learning model may allow the development of a digital image optimization algorithm that has learned and progressed from experience without being explicitly programmed, as will be discussed. In one example, the machine-learning model may be trained using a "red boost" library of digital images from past surgeries as training images. The red boost library may contain images of poor red reflux of eyes and bright red reflux of eyes. By training on the red boost library, the machine-learning model may be able to predict an optimized digital image of the eye 191. The digital image optimization algorithm may alternatively be an algorithm that utilizes another image enhancement technique, for example, interpolation or multi-exposure image noise reduction.

The digital image optimization algorithm may at least partially reduce instrument glare 110, optical aberration 120, vitreous fog 130, or any combination thereof, in a digital image of the eye 101 captured by the camera 150 to generate the optimized digital image of the eye 191. The optimized digital image of the eye 191 may have less instrument glare 110, less optical aberration 120, less vitreous fog 130, or any combination thereof than a digital image of the eye 101 captured by the camera 150 that has not had a digital optimization algorithm applied.

The processor 180 may include, for example, a field-programmable gate array (FPGA), a microprocessor, a microcontroller, a digital signal processor (DSP), a graphics processing unit (GPU), an application specific integrated circuit (ASIC), or any other digital or analog circuitry configured to interpret and/or execute program instructions and/or process data.

The processor 180 may include any physical device able to store and/or execute instructions. The processor 180 may execute processor instructions to implement at least a portion of one or more systems, one or more flow charts, one or more processes, and/or one or more methods described herein. For example, the processor 180 may execute instructions to produce a digital image of the eye 101. The processor 180 may be configured to receive instructions from the memory medium 181. In one example, the processor 180 may include the memory medium 181. In another example, the memory medium 181 may be external to the processor 180. The memory medium 181 may store the instructions. The instructions stored by the memory medium 181 may be executable by the processor 180 and may be configured, coded, and/or encoded with instructions in accordance with at least a portion of one or more systems, one or more flowcharts, one or more methods, and/or one or more processes described herein. The memory medium 181 may store instructions that may be executable by the processor 180 to apply a digital image optimization algorithm to a digital image of the eye 101 captured by the camera 150.

A FPGA may be may be configured, coded, and/or encoded to implement at least a portion of one or more systems, one or more flow charts, one or more processes, and/or one or more methods described herein. For example, the FPGA may be configured, coded, and/or encoded to produce a digital image of the eye 101. An ASIC may be may be configured to implement at least a portion of one or more systems, one or more flow charts, one or more processes, and/or one or more methods described herein. For example, the ASIC may be configured, coded, and/or encoded to produce a digital image of the eye 101. A DSP may be may be configured, coded, and/or encoded to implement at least a portion of one or more systems, one or more flow charts, one or more processes, and/or one or more methods described herein. For example, the DSP may be configured, coded, and/or encoded to produce a digital image of the eye 101.

A single device may include the processor 180 and the image processing system 170, or the processor 180 may be separate from the image processing system 170. In one example, a single computer system may include the processor 180 and the image processing system 170. In another example, a device may include integrated circuits that may include the processor 180 and the image processing system 170. Alternatively, the processor 180 and the image processing system 170 may be incorporated into a surgical console.

The processor 180 may interpret and/or execute program instructions and/or process data stored in the memory medium 181. The memory medium 181 may be configured in part or whole as application memory, system memory, or both. The memory medium 181 may include any system, device, or apparatus configured to hold and/or house one or more memory devices. Each memory device may include any system, any module or any apparatus configured to retain program instructions and/or data for a period of time (e.g., computer-readable media). One or more servers, electronic devices, or other machines described may include one or more similar such processors or memories that may store and execute program instructions for carrying out the functionality of the associated machine.

The digital image optimization system 100 may include a digital display 190. The digital display 190 may include any type of screen or projector able to display a digital image of the eye 101 with sufficient resolution to be usable in ophthalmic surgery. For instance, it may include any type of screen or projector used in connection with ophthalmic surgery, including displays of the type used in conventional vitreoretinal surgical systems that present digital images. The digital display 190 may display the optimized digital image of the eye 191. This may improve digital visualization for ophthalmic surgery by providing a digital image of the eye with less instrument glare 110, less optical aberration 120, less vitreous fog 130, or any combination thereof than a digital image of the eye 101 that is not optimized. The digital display 190 may display a digital image that is a combined digital image of a digital image of the eye 101 and the optimized digital image of the eye 191. The combined digital image may be generated by the processor 180. The proportion of the digital image of the eye 101 and the optimized digital image of the eye 191 displayed in the combined image may be controlled by the surgeon, for example, using a slider bar controlled by a controller 192. In this way, the surgeon can control the degree to which the optimized digital image is used for visualization during surgery.

The digital display 190 may display a single image, or two images for stereoscopic viewing. The digital display 190 may be a digital display, a screen, a head up display, a head mounted display, or any combination thereof, and may also include multiple displays. The digital display 190 may be a flat panel display or an ultra-high-definition 3D flat panel display. The digital display 190 may be a 3D organic light-emitting diode (OLED) surgical display. The images displayed on the digital display 190 may be viewed through a pair of passive, circular polarized glasses. The digital display 190 may be a picture-in-picture display. The digital display 190 may be a component of a Digitally Assisted Vitreoretinal Surgery ("DAVS") system, or may be a component of an NGENUITY® 3D Visualization System (Novartis AG Corp., Switzerland).

The digital display 190 may display the optimized digital image of the eye 191 generated by the processor 180 or another processor and other information generated by the processor 180 or another processor. Such information may include graphic or textual information, such as surgical parameters, surgical modes, flow rates, intraocular pressure, endoscopic video, OCT images, warnings, digital images, color coding or augmented reality information. The processor 180 may reformat video made using the camera 150 for display on the digital display 190, which may be viewed with circularly polarized glasses, digital oculars, or using a head mounted display.

A digital optimization algorithm may be generated using a machine-learning model. The machine-learning model may be trained using a plurality training images, as will be discussed. The training images may include digital images captured at the beginning of surgery and digital images captured at the conclusion of surgery, as depicted in FIGS. 2A-D. A digital image captured at the beginning of a surgery may provide the worst visualization of an eye. This may be because the digital image includes instrument glare 110, optical aberration 120, vitreous fog 130, or any combination thereof. A digital image of the same eye captured at the conclusion of the surgery may provide the best visualization of the eye. This may be because many of the sources of noise or distortion, such as instrument glare 110, optical aberration 120, vitreous fog 130, or any combination thereof, have been removed. Thus, training a machine-learning model using a plurality of digital images captured at the beginning of a surgery and a plurality of corresponding digital images of the eye captured at the conclusion of the surgery over a plurality of eyes may generate a digital optimization algorithm for predicting a digital image captured at the conclusion of surgery from an input digital image captured at the beginning of a surgery. If necessary, the digital image of the eye captured at the beginning of surgery may be aligned with the digital image of the eye captured at the conclusion of surgery using the optic disk, the retina arcade, or a combination thereof. This may provide a register with which to align and compare the images.

Figure 2A:
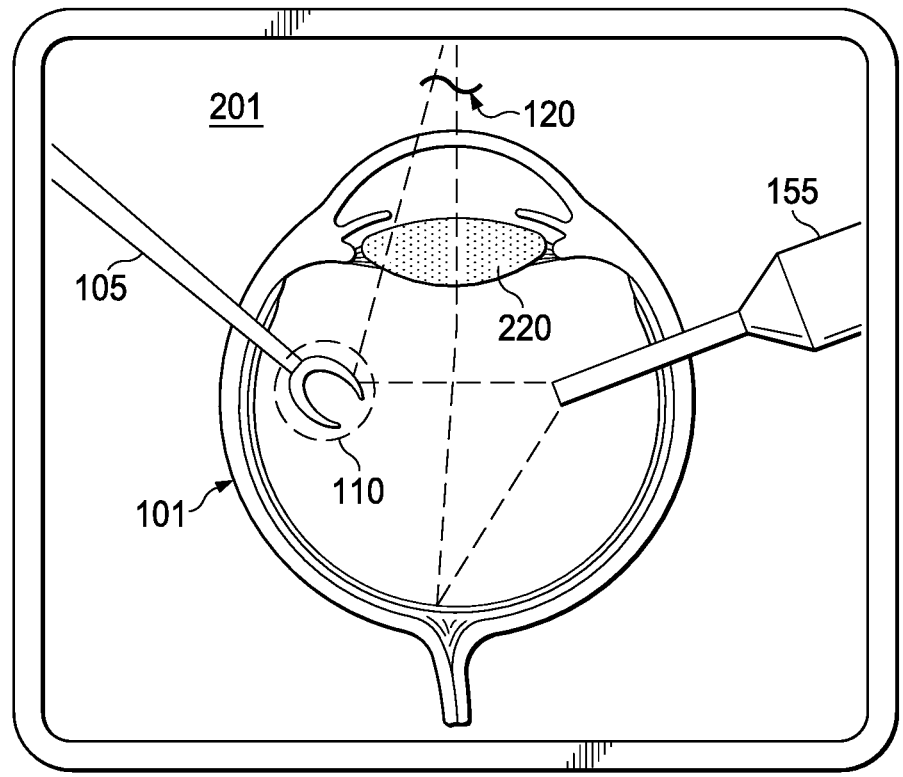
FIGS. 2A-2D are schematic representations of training images.

For example, a digital image of the eye at the beginning of surgery 201 may be a digital image of the eye 101 captured by the camera 150 at the beginning of a surgery, as depicted in FIG. 2A. The digital image of the eye at the beginning of surgery 201 may include instrument glare 110 caused, for example, by light emitted by the visible light illumination source 155 and reflected off the surgical instrument 105. Instrument glare 110 may appear as noise or distortion in digital image of the eye at the beginning of surgery 201. The digital image of the eye at the beginning of surgery 201 may also include optical aberration 120 caused by light emitted by the visible light illumination source 155 and reflected off the interior of the eye 101. Optical aberration 120 may be caused, for example, by a cloudy lens 220. Optical aberration 120 may reduce the contrast, sharpness, clarity, and dynamic range of the digital image of the eye at the beginning of surgery 201.

Figure 2B:
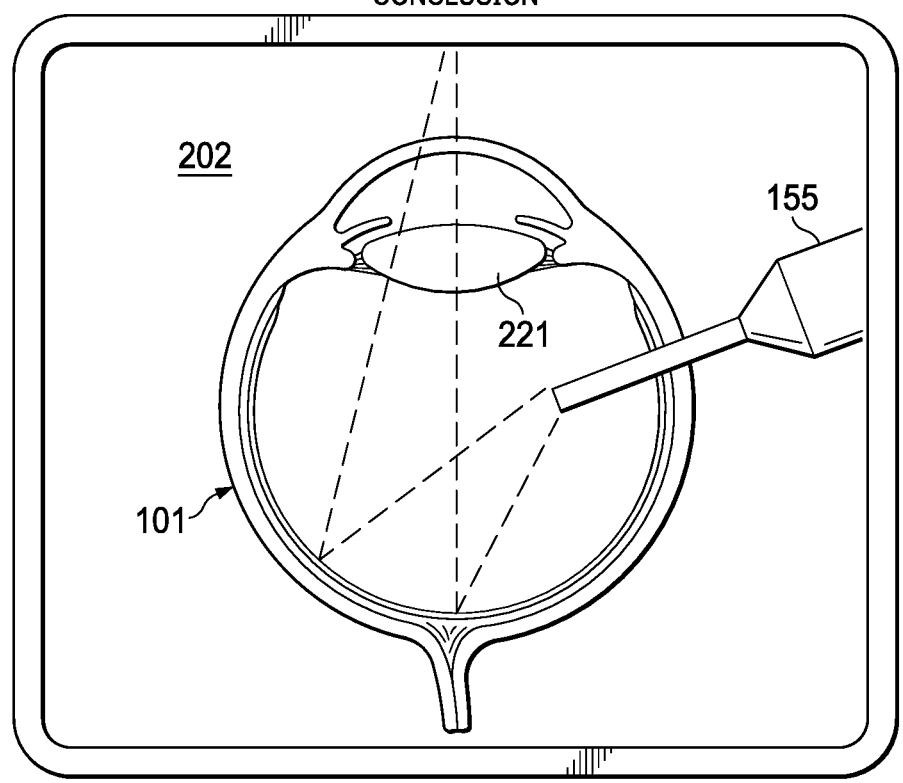

A digital image of the eye at the conclusion of surgery 202 may be a digital image of the eye 101 captured by the camera 150 at the conclusion of surgery, as depicted in FIG. 2B. At the conclusion of surgery, the surgical instrument 105 may have at least in part been removed from the eye 101. Accordingly, the digital image of the eye at the conclusion of surgery 202 may have less instrument glare 110, or may not include instrument glare 110. At the conclusion of the surgery, the cloudy lens 220 may have at least in part been replaced with an artificial lens 221. Accordingly, the digital image of the eye at the conclusion of surgery 202 may have less optical aberration 120, or may not include optical aberration 120. The digital image of the eye at the conclusion of surgery 202 may have improved contrast, sharpness, clarity, and dynamic range, and may have decreased noise, distortion, and vignetting as compared to the digital image of the eye at the beginning of surgery 201.

Figure 2C:
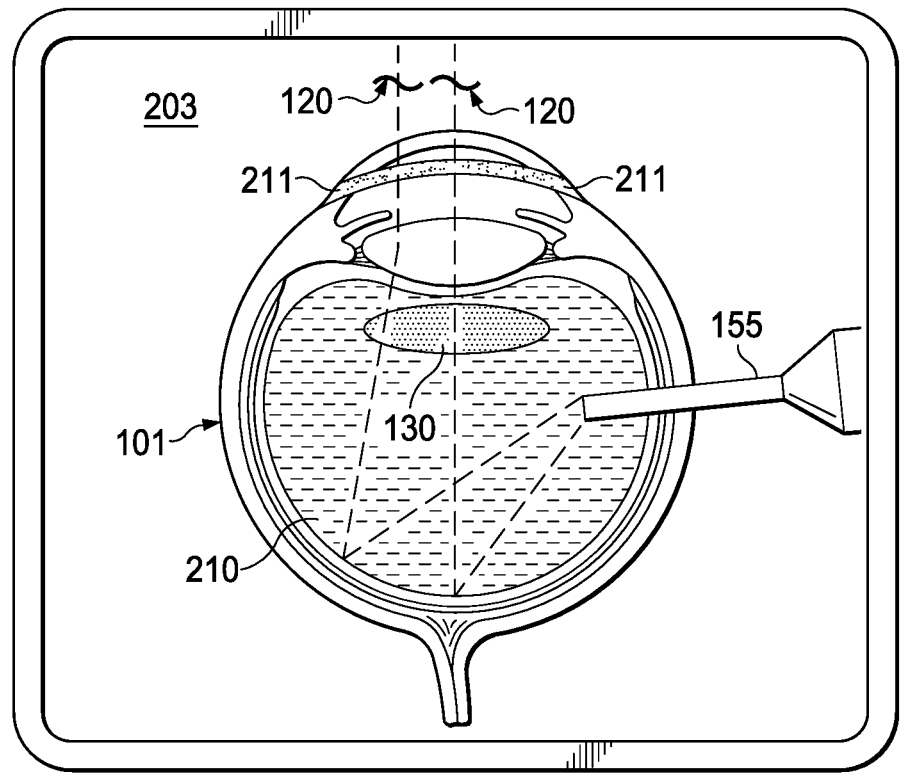

In another example, a digital image of the eye at the beginning of surgery 203 may be a digital image of the eye 101 captured by the camera 150 at the beginning of a surgery, as depicted in FIG. 2C. The digital image of the eye at the beginning of surgery 203 may include vitreous fog 130 caused by light emitted by the visible light illumination source 155 and reflected off a vitreous 210. Vitreous fog 130 may appear as noise or distortion in the digital image of the eye at the beginning of surgery 203. The digital image of the eye at the beginning of surgery 203 may also include optical aberration 120 caused by light emitted by the visible light illumination source 155 and reflected off the interior of the eye 101. Optical aberration 120 may be caused by blood 211. Optical aberration 120 may reduce the contrast, sharpness, clarity, and dynamic range of the digital image of the eye at the beginning of surgery 203.

Figure 2D:
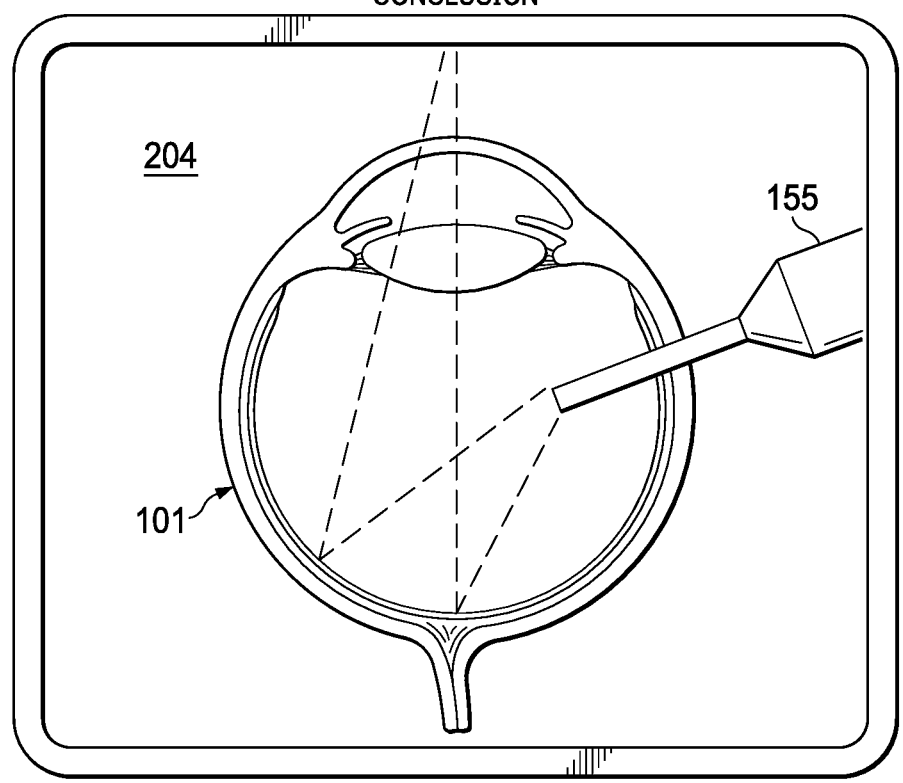

A digital image of the eye at the conclusion of surgery 204 may be a digital image of the eye 101 captured by the camera 150 at the conclusion of the surgery, as depicted in FIG. 2D. At the conclusion of the surgery, the vitreous 210 may have at least in part been removed from the eye 101. Accordingly, the digital image of the eye at the conclusion of surgery 204 may include less vitreous fog 130, or may not include vitreous fog 130. At the conclusion of the surgery, blood 211 may have also at least in part been removed. Accordingly, the digital image of the eye at the conclusion of surgery 204 may include less optical aberration 120, or may not include optical aberration 120. The digital image of the eye at the conclusion of surgery 204 may have improved contrast, sharpness, clarity, and dynamic range, and may have decreased noise, distortion, and vignetting as compared to the digital image of the eye at the beginning of surgery 203.

A plurality of digital images of the eye at the beginning of surgery and a plurality of digital images of the same eyes at the conclusion of surgery may be used as input images and output images, respectively, in a set of training images for training a machine-learning model. For example, an input image may be the digital image of the eye at the beginning of surgery 201 and an output image may be the digital image of the eye at the conclusion of surgery 202. A machine-learning model may be trained based on extracting features from the input image and learning a relationship function between the extracted features and the differentials between the input image and the output image, as will be discussed. The trained machine-learning model may be used as a digital image optimization algorithm.

The digital image optimization algorithm may generate processor instructions using the memory medium 181 to be executed on the processor 180 to optimize a digital image of the eye at the beginning of surgery, for example the digital image of the eye at the beginning of surgery 201 or the digital image of the eye at the beginning of surgery 203. The processor 180 may execute instructions to produce the optimized digital image of the eye 191. The optimized digital image of the eye 191 may have improved image quality that is comparable to that of a digital image of the eye at the conclusion of surgery, for example that is comparable to that of the digital image of the eye at the conclusion of surgery 202 or the digital image of the eye at the conclusion of surgery 204. The optimized digital image of the eye 191 may have improved contrast, improved sharpness, improved clarity, improved dynamic range, decreased noise, decreased distortion, decreased vignetting, or any combination thereof, as compared to the digital image of the eye 101.

Figure 3:
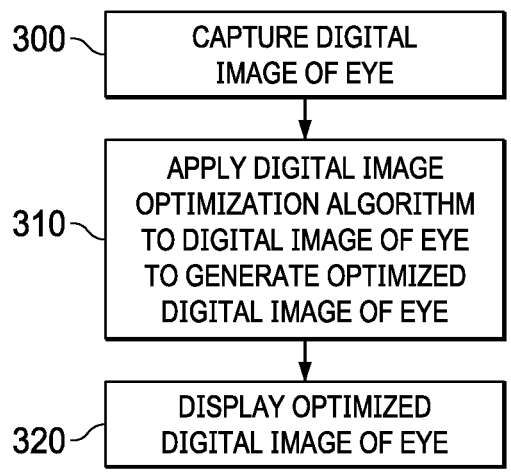
FIG. 3 is a flow diagram illustrating a method of optimizing a digital image of an eye to improve digital visualization for ophthalmic surgery.

FIG. 3 presents a flow chart for a method of optimizing a digital image of the eye to improve digital visualization for ophthalmic surgery. In step 300, a digital image of an eye is captured. The digital image of the eye may be captured by a camera such as the camera 150. The digital image of the eye may be captured at the beginning of surgery, and may be a digital image such as the digital image of the eye at the beginning of surgery 201, or the digital image of the eye may be captured during surgery. The digital image of the eye may have instrument glare, such as instrument glare 110, optical aberration, such as optical aberration 120, vitreous fog, such as vitreous fog 130, or any combination thereof. In step 310, a digital image optimization algorithm is applied to the digital image of the eye to generate an optimized digital image of the eye, such as the optimized digital image of the eye 191. The digital image optimization algorithm may be a trained machine-learning model. In step 320, the optimized digital image of the eye is displayed on a digital display, such as the digital display 190.

Figure 4:
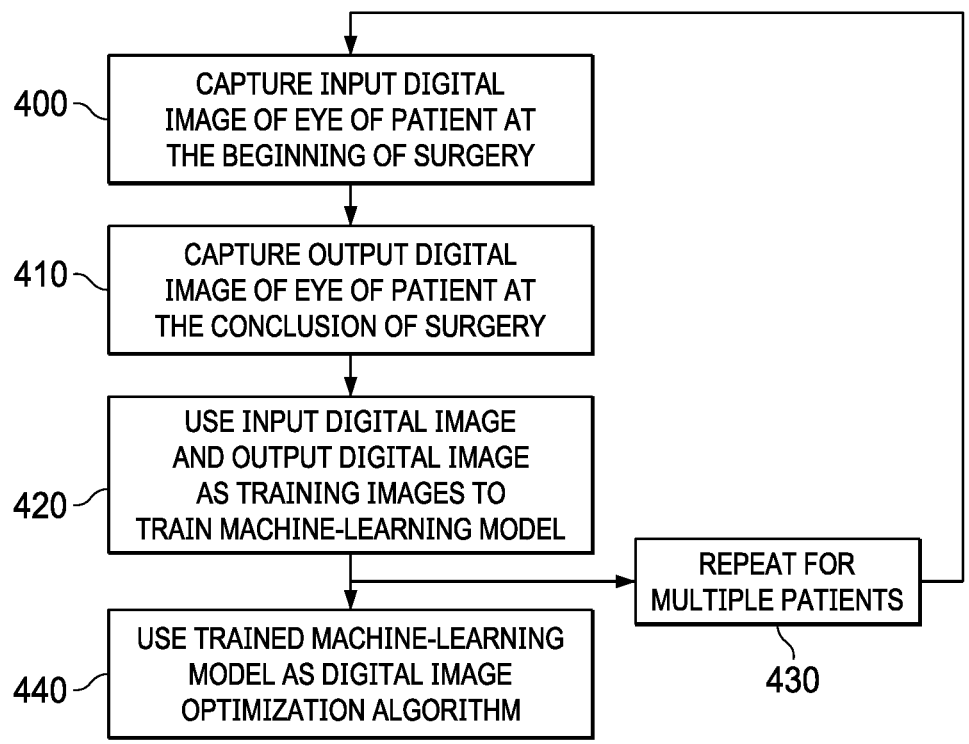
FIG. 4 is a flow diagram illustrating a method of generating a digital image optimization algorithm using a machine-learning model to improve digital visualization for ophthalmic surgery.

FIG. 4 presents a flow chart for a method of generating a digital image optimization algorithm using a machine-learning model to improve digital visualization for ophthalmic surgery. In step 400, an input digital image of the eye is captured at the beginning of surgery, such as the digital image of the eye at the beginning of surgery 201 captured by the camera 150. In step 410, an output digital image of the same eye is captured at the conclusion of surgery, such as the digital image of the eye at the conclusion of surgery 202 captured by the camera 150. In step 420, the input digital image of the eye at the beginning of surgery and the output digital image of the eye captured at the conclusion of surgery are used as an input image and an output image respectively, in a set of training images to train a machine-learning model. In step 430, steps 400-420 are repeated for a plurality of input images and output images for multiple patients. These images may be collected from a wide range of surgeons and ophthalmic hospitals. The plurality of input images and output images may be used to train a machine-learning model to predict an output image, for example, a digital image of the eye at the conclusion of surgery, when provided with only an input image, for example, a digital image of the eye at the beginning of surgery. In step 440, the trained machine-learning model may be used as a digital image optimization algorithm to improve a digital image of the eye.

Figure 5:
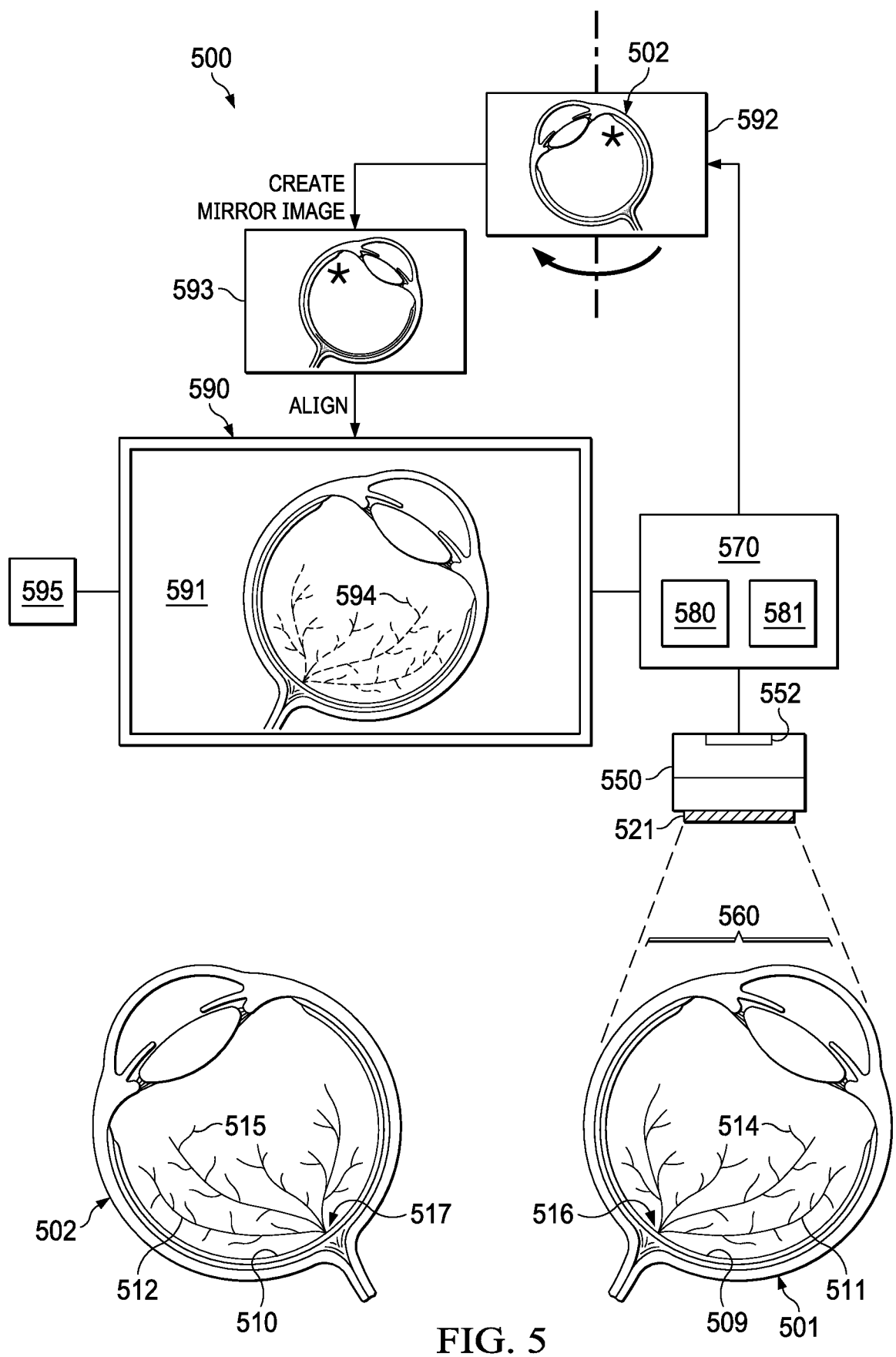
FIG. 5 is a schematic representation of a digital image optimization system including a camera, an image processing system, and a digital display.

In an alternative example, a digital image optimization system 500 may improve digital visualization for ophthalmic surgery by providing a retina arcade alignment template, as depicted in FIG. 5. The retina arcade may include the vascular architecture of the retina. The retina arcade may include temporal arcade vessels. By aligning the retina arcade, digital images of the same eye captured at different stages during surgery may be aligned. Alternatively, an alignment of the digital mirror image of a retina arcade of a fellow eye 502 (a healthy eye that is not being operated on) to a digital image of an operative eye 501 of the same patient may provide a retina arcade alignment template during surgery. This may provide an optimized digital image of the operative eye. The fellow eye may be a right eye and the operative eye may be a left eye of the same patient. Alternatively, the fellow eye may be the right eye and the operative may be the left eye of the same patient.

For example, during a vitrectomy, digital visualization may be improved by use of an overlaid and aligned digital mirror image of the retina arcade of the fellow eye to the digital image of the operative eye to provide a retina arcade alignment template for retina reattachment. This may at least in part prevent cyclo-distortion following a vitrectomy to correct retinal detachment. The pattern of the retina arcade of the fellow eye may be the most similar to the pattern of the retina arcade of the operative eye compared to any other eye. The alignment may be done intra-operatively using a digital visualization system, as shown in FIG. 5. The visualization system may be a 2D or a 3D visualization system.

The digital image optimization system 500 may include a camera 550, an image processing system 570, and a digital display 590. The camera 550 may be a digital camera, an HDR camera, a 3D camera, or any combination thereof. The camera 550 may be a component of an NGENUITY® 3D Visualization System (Novartis AG Corp., Switzerland). The camera 550 may also be a camera coupled to a microscope. The camera 550 may replace the oculars on a microscope, and may be a fifth-generation image capture module (ICM5) 3D surgical camera. The camera 550 may be configured to provide a stereoscopic digital image of the operative eye 501 or the fellow eye 502 (not shown). The camera 550 may include a lens 521. The lens 521 may also be an opto-mechanical focus lens, a manual focus lens, or any combination thereof. The camera 550 may also include at least one image sensor 552, which may be a charge-coupled device (CCD) sensor or a complementary metal-oxide semiconductor (CMOS) sensor. The camera 550 may be a monochrome camera, or may be a color camera, and the at least one image sensor 552 may be a monochrome image sensor or may be a color image sensor. The at least one image sensor 552 may be an image sensor with a color filter array, for example a Bayer filter, or may be an image sensor without a color filter array. Alternatively, images captured by the camera 550 may be optical coherence tomography (OCT) images, multi/hyper spectral images, ultrasound images, or any combination thereof.

A digital image of the operative eye 501 or the fellow eye 502 captured by the camera 550 may include a field of view 560. The field of view 560 may include a close-up view of the operative eye 501 or the fellow eye 502, and may include a higher magnification view of the retina arcade, or other areas of the operative eye 501 or the fellow eye 502.

Before surgery, the camera 550 may capture a template digital image 592 of the fundus of the fellow eye 502. The template digital image 592 may include a digital image of the retina of the fellow eye 510, the central retina vein of the fellow eye 512, the retina arcade of the fellow eye 515, the optic disk of the fellow eye 517, or any combination thereof. During surgery, the camera 550 may capture a working digital image 591 of the fundus of the operative eye 501. The working digital image 591 may have an equivalent field of view 560 of the operative eye 501 to the field of view 560 of the template digital image 592 of the fellow eye 502. The working digital image 591 may include a digital image of the retina of the operative eye 509, the central retina vein of the operative eye 511, the retina arcade of the operative eye 514, the optic disk of the operative eye 516, or any combination thereof.

A digital image captured by camera 550 may be processed by the image processing system 570. The image processing system 570 may include a processor 580. The camera 550 may detect light reflected off the interior of the operative eye 501 or the fellow eye 502 into the lens 521 using the at least one image sensor 552, which may send a signal corresponding to the detected light to the processor 580. The processor 580 may execute instructions to produce a working digital image 591 of the operative eye 501, a template digital image 592 of the fellow eye 502, or a combination thereof. The image processing system 570 may also include a memory medium 581. The working digital image 591, the template digital image 592, or a combination thereof, may be stored in the memory medium 581.

The processor 580 may execute instructions to create a digital mirror image 593 of the template digital image 592. The processor 580 may execute instructions to align the digital mirror image 593 with the working digital image 591 to generate a retina arcade alignment template 594. The processor 580 may execute instructions to align the digital mirror image 593 with the working digital image 591 by aligning the optic disk of the fellow eye 517 with the optic disk of the operative eye 516, by aligning the central retina vein of the fellow eye 512 with the central retina vein of the operative eye 511, or a combination thereof. The processor 580 may also execute instructions to align the digital mirror image 593 with the working digital image 591 by aligning arterial vein crossings (not shown), branch veins (not shown), or a combination thereof. The processor 580 may be similar to the processor 180.

The digital display 590 may include any type of screen or projector able to display a digital image of the operative eye 501 with sufficient resolution to be usable in ophthalmic surgery. For instance, it may include any type of screen or projector used in connection with ophthalmic surgery, including displays of the type used in conventional vitreoretinal surgical systems that present digital images. The digital display 590 may be similar to the digital display 190.

The digital display 590 may display the working digital image 591, the template digital image 592, the digital mirror image 593, the retina arcade alignment template 594, or any combination thereof. The digital display 590 may display the working digital image 591 and an overlay of the retina arcade alignment template 594. This may improve digital visualization for ophthalmic surgery by providing the retina arcade alignment template 594 for reattachment of a retina. The working digital image 591 with an overlay of the retina arcade alignment template 594 may represent an optimized digital image of the eye as compared to the working digital image 591 alone. The digital display 590 may display a digital image that is a combined digital image of the retina arcade alignment template 594 and the working digital image 591. The combined digital image may be generated by the processor 580. The proportion of the working digital image 591 and the retina arcade alignment template 594 displayed in the combined image may be controlled by the surgeon, for example, using a slider bar controlled by a controller 595. In this way, the surgeon may control the degree to which the retina arcade alignment template 594 is used for visualization during surgery.

The digital display 590 may display a single image, or two images for stereoscopic viewing. The digital display 590 may be a digital display, a screen, a head up display, a head mounted display, or any combination thereof, and may also include multiple displays. The digital display 590 may be a flat panel display or an ultra-high-definition 3D flat panel display. The digital display 590 may be a 3D organic light-emitting diode (OLED) surgical display. The images displayed on the digital display 590 may be viewed through a pair of passive, circular polarized glasses. The digital display 590 may be a component of a Digitally Assisted Vitreoretinal Surgery ("DAVS") system, or may be a component of an NGENUITY® 3D Visualization System (Novartis AG Corp., Switzerland).

Alternatively, the digital display 590 may be a picture-in-picture display, and may display at least two digital images concurrently. For example, the digital display 590 may display the working digital image 591 and the retina arcade alignment template 594 concurrently. The working digital image 591 may be displayed as a main image and the retina arcade alignment template 594 may be displayed in an inset position. Alternatively, the working digital image 591 may be displayed as the main image and the working digital image 591 with an overlay of the retina arcade alignment template 594 may be displayed in an inset position.

The digital display 590 may display the working digital image 591, the template digital image 592, the digital mirror image 593, the retina arcade alignment template 594, or any combination thereof generated by the processor 580 or another processor and other information generated by the processor 580 or another processor. Such information may include graphic or textual information, such as surgical parameters, surgical modes, flow rates, intraocular pressure, endoscopic video, OCT images, warnings, digital images, color coding or augmented reality information. The processor 580 may reformat video made using the camera 550 for display on the digital display 590, which may be viewed with circularly polarized glasses, digital oculars, or using a head mounted display.

The digital image optimization system 500 may be used to optimize a digital image of the eye by providing the retina arcade alignment template 594 for retina reattachment after a vitrectomy. The image processing system 570 may detect any misalignment of the retina as it is being reattached using the retina arcade alignment template 594. A misalignment of the retina may be adjusted using, for example, a soft tip cannula. The degree of misalignment may also be quantified using the image processing system 570. The degree of misalignment may be quantified mathematically, graphically, or a combination thereof, to inform on a surgeon's assessment of the retina reattachment. Mathematical information, graphical information, or a combination thereof, may further be used by the digital image optimization system 500 to suggest surgical alignment movements to the surgeon.

Figure 6:
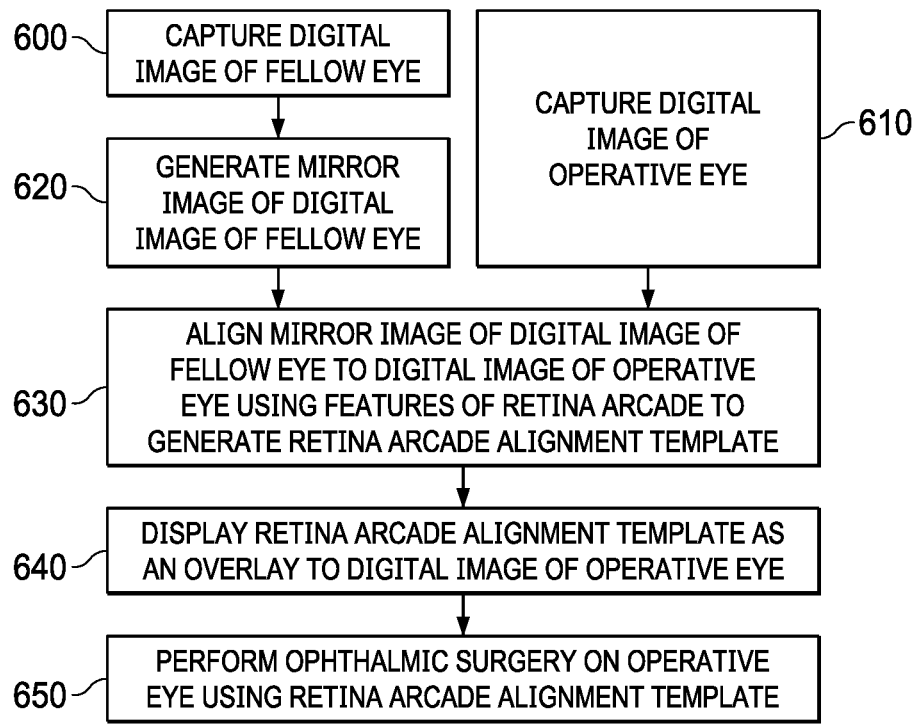
FIG. 6 is a flow diagram illustrating a method of optimizing a digital image of an eye by using a retina arcade alignment template to improve digital visualization for ophthalmic surgery.

FIG. 6 presents a flow chart for a method of optimizing a digital image of the eye to improve digital visualization for ophthalmic surgery by using a retina arcade alignment template. In step 600, a digital image of a fellow eye, such as the template digital image 592, is captured before surgery. In step 610, a digital image of an operative eye, such as the working digital image 591, is captured during surgery. In step 620, a mirror image of the digital image of the fellow eye, such as the digital mirror image 593, is generated. In step 630, the mirror image of the digital image of the fellow eye is aligned to the digital image of the operative eye using features of the retina arcade to generate a retina arcade alignment template, such as the retina arcade alignment template 594. For example, the digital images may be aligned by aligning the optic disk, the central retina vein, arterial vein crossings, branch veins, or any combination thereof. The digital images may be aligned in 2D or 3D. In step 640, the retina arcade alignment template is displayed as an overlay to the digital image of the operative eye. In step 650, ophthalmic surgery is performed on the operative eye using the retina arcade alignment template. An example of an ophthalmic procedure that would benefit from improved digital visualization using a retina arcade alignment template may include a reattachment of a retina following a vitrectomy.

Figure 7:
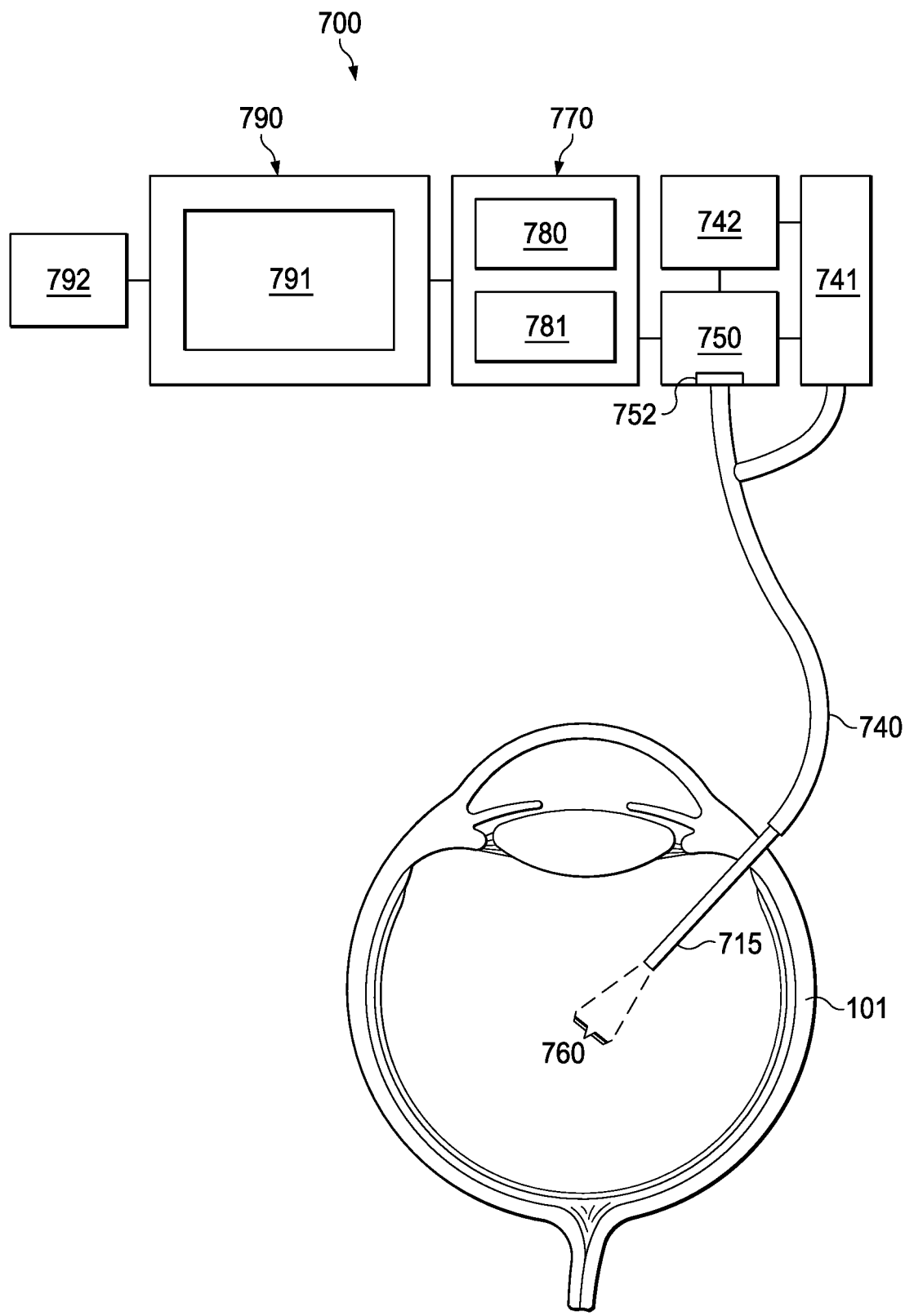
FIG. 7 is a schematic representation of a digital image optimization system including an endoscope, an optical fiber, an optical fiber light source, a camera, an image processing system, and a digital display.

In another alternative example, a digital image optimization system 700 may improve digital visualization for ophthalmic surgery by providing super resolution optimization of an endoscope digital image of the eye, as depicted in FIG. 7. This may improve digital visualization for ophthalmic surgery by increasing the resolution of a low-resolution digital image, for example, an endoscope digital image of about 30,000 pixels. This may allow the low-resolution digital image to be displayed on a high-resolution digital display, for example a digital display of over one million pixels, with improved image quality.

Referring now to FIG. 7, the digital image optimization system 700 may include an endoscope 715, an optical fiber 740, an optical fiber light source 741, a camera 750, an image processing system 770, and a digital display 790. The image processing system 770 may further include a processor 780 and a memory medium 781. The digital image optimization system 700 may provide an optimized endoscope digital image 791 of the eye 101 to improve digital visualization for ophthalmic surgery.

The endoscope 715 may be inserted into the eye 101. The endoscope 715 may be positioned such that a desired field of view 760 of the interior of the eye 101 is captured in the optimized endoscope digital image 791. The optical fiber 740 may be positioned within the endoscope 715, and may extend to the tip of the endoscope 715. The optical fiber 740 may include about 30,000 image fibers. Alternatively, the optical fiber 740 may include any suitable number of image fibers to provide the desired optimized endoscope digital image 791 of the eye 101 using the endoscope 715.

The optical fiber 740 may be coupled to the optical fiber light source 741. The optical fiber light source 741 may be a laser source, a narrowband laser source, a broadband laser source, a supercontinuum laser source, an incandescent light bulb, a halogen light bulb, a metal halide light bulb, a xenon light bulb, a mercury vapor light bulb, a light emitting diode (LED), a laser engine, other suitable sources, or any combination thereof. Light reflected off the interior of the eye 101 may propagate through the image fibers in the optical fiber 740, and may be detected by the camera 750. The digital image optimization system 700 may also include an eyepiece for the endoscope 715 in addition to the camera 750 (not shown).

The camera 750 may include at least one camera sensor 752. The at least one camera sensor 752 may be a complementary metal-oxide semiconductor (CMOS) sensor or a charge-coupled device (CCD) sensor. The camera 750 may be a monochrome camera, or may be a color camera, and the at least one camera sensor 752 may be a monochrome image sensor or may be a color image sensor. The at least one camera sensor 752 may capture a digital image using light propagated by the optical fiber 740, which may be light reflected off the interior of the eye 101. The at least one camera sensor 752 may capture a digital image of the eye 101, which may be an endoscope digital image of eye 101.

The optical fiber 740, the optical fiber light source 741, the camera 750, and the at least one camera sensor 752 may be controlled by a control device 742. For example, the control device 742 may adjust the intensity of the optical fiber light source 741, the sensitivity of the at least one camera sensor 752, or any combination thereof. Although FIG. 7 illustrates a single endoscope 715 in the digital image optimization system 700, the digital image optimization system 700 may include multiple endoscopes 715, optical fibers 740, cameras 750 and camera sensors 752. In this case, the multiple endoscopes 715 may be inserted into multiple positions of the eye 101 to provide multiple endoscope digital images of the eye.

The digital image optimization system 700 may include the image processing system 770. Digital images captured by the at least one camera sensor 752 may be processed by the image processing system 770. The image processing system 770 may include the processor 780. The camera 750 may detect light reflected off the interior of the eye 101 and propagated by the optical fiber 740 using the at least one camera image sensor 752, and send a signal corresponding to the detected light to the processor 780. The processor 780 may execute instructions to produce an endoscope digital image of the eye 101.

The endoscope digital image of the eye 101 captured by the camera 750 may be processed by the image processing system 770. The image processing system 770 may also include the memory medium 781. The endoscope digital image of the eye 101 may be stored in the memory medium 781. The processor 780 may execute instructions to apply an endoscope digital image optimization algorithm to the endoscope digital image of the eye 101 to produce an optimized endoscope digital image of the eye 791. The optimized endoscope digital image of the eye 791 may be a super resolution digital image of the eye. A super resolution digital image may be generated by upscaling a low-resolution endoscope digital image of the eye to produce a high-resolution endoscope digital image of the eye. Examples of methods that may be used to generate the optimized endoscope digital image of the eye 791 include, but are not limited to, interpolation, multi-exposure image noise reduction, machine learning, deep learning, or any combination thereof, as will be described. Use of an interpolation method, for example, may generate the optimized endoscope digital image of the eye 791 faster compared to use of a machine learning method. Use of a machine learning method, for example, may generate an improved optimized endoscope digital image of the eye 791 compared to use of an interpolation method.

The endoscope digital image optimization algorithm may generate the optimized endoscope digital image of the eye 791 using interpolation. For example, the endoscope digital image optimization algorithm may generate the optimized endoscope digital image of the eye 791 by replacing a lower quality subject pixel in the endoscope digital image of the eye 101 with an adjacent pixel of higher contrast, higher sharpness, higher clarity, or any combination thereof. A lower quality subject pixel may be a pixel that does not display an expected color, permanently displays a particular color, is permanently white, is permanently black, permanently displays as a "hot pixel", is a dead pixel, or any combination thereof. The subject pixel may be modified to optimize pixel image quality without any noticeable image distortion as the area being modified is generally small. Examples of interpolation methods that may be included in the endoscope digital image optimization algorithm may include, but are not limited to, nearest-neighbor interpolation, linear interpolation, bilinear interpolation, bicubic interpolation, anisotropic filtering, or any combination thereof.

In another example, the endoscope digital image optimization algorithm may generate the optimized endoscope digital image of the eye 791 using multi-exposure image noise reduction. The endoscope 715 may be dynamically scanned by the surgeon over an area of interest such that a plurality of endoscope digital images of the eye 101 may be combined to give a single optimized endoscope digital image of the eye 791.

The endoscope digital image optimization algorithm may be a trained machine-learning model. The machine-learning model may be trained using a plurality of training images, as will be discussed, which may be a plurality of endoscope digital images of the eye that have been successfully optimized using an image processing method, such as one of the imaging processing methods described above. For example, optimization of the endoscope digital image of the eye may be deemed successful if the surgeon successfully completed surgery using the optimized endoscope digital image of the eye.

In a further example, the endoscope digital image optimization algorithm may generate the optimized endoscope digital image of the eye 791 using a deep learning method. For example, the endoscope digital image optimization algorithm may utilize single image super-resolution (SISR) using deep learning. SISR may be the process of generating a high-resolution digital image from a single low-resolution digital image. In one example, a very-deep super-resolution (VDSR) neural network may be used for SISR. The VDSR neural network may learn the mapping between a low-resolution digital image and a high-resolution digital image. In general, a low-resolution digital image and a high-resolution digital image of the same subject may have similar image content. A low-resolution digital image may differ from a high-resolution digital image in high-frequency details. The difference in pixel values between a high-resolution image and a low-resolution image of the same subject that has been upscaled to match the size of the high-resolution image may be called a residual image. The VDSR neural network may learn to estimate a residual image from a set of training images of low-resolution and high-resolution pairs of endoscope digital images of the eye. A high-resolution endoscope digital image of the eye may be reconstructed from a low-resolution endoscope digital image of the eye by adding the estimated residual image to an upscaled low-resolution endoscope digital image of the eye. By using a VDSR neural network, SISR may recover a high-resolution endoscope digital image of the eye 101 from a low-resolution endoscope digital image of the eye 101. The high-resolution endoscope digital image of the eye 101 may be the optimized endoscope digital image of the eye 791. As an alternative, other suitable neural networks may be used by the endoscope digital image optimization algorithm to perform SISR.

The endoscope digital image optimization algorithm may at least partially reduce noise, increase resolution, improve digital image quality, or any combination thereof of the endoscope digital image of the eye 101 captured by the camera 750. For example, the optimized endoscope digital image of the eye 791 may have increased contrast, sharpness, clarity, dynamic range, or any combination thereof compared to an endoscope digital image of the eye 101 captured by the camera 750 that has not had an endoscope digital optimization algorithm applied. Although the digital image optimization system 700 includes the endoscope 715, a super resolution digital image of the eye may equally be provided for a digital image of the eye captured with a camera, for example, a camera such as the camera 150 or the camera 550.

The optimized endoscope digital image 791 may be displayed on the digital display 790. The digital display 790 may include any type of screen or projector able to display the optimized endoscope digital image 791 with sufficient resolution to be usable in ophthalmic surgery. For instance, it may include any type of screen or projector used in connection with ophthalmic surgery, including displays of the type used in conventional vitreoretinal surgical systems that present digital images. The digital display 790 may display the optimized endoscope digital image 791 concurrently with another digital image of the eye 101, for example, the optimized digital image of the eye 191. The digital display 790 may display a digital image that is a combined digital image of an endoscope digital image of the eye 101 and the optimized endoscope digital image 791. The combined digital image may be generated by the processor 780. The proportion of the endoscope digital image of the eye 101 and the optimized endoscope digital image of the eye 791 displayed in the combined image may be controlled by the surgeon, for example, using a slider bar controlled by a controller 792. In this way, the surgeon may control the degree to which the optimized endoscope digital image 791 is used for visualization during surgery.

The digital display 790 may display a single image, or two images for stereoscopic viewing. The digital display 790 may be a digital display, a screen, a head up display, a head mounted display, or any combination thereof, and may also include multiple displays. The digital display 790 may be a flat panel display or an ultra-high-definition 3D flat panel display. The digital display 790 may be a 3D organic light-emitting diode (OLED) surgical display. The images displayed on the digital display 790 may be viewed through a pair of passive, circular polarized glasses. The digital display 790 may be a component of a Digitally Assisted Vitreoretinal Surgery ("DAVS") system, or may be a component of an NGENUITY® 3D Visualization System (Novartis AG Corp., Switzerland).

Alternatively, the digital display 790 may be a picture-in-picture display, and may display at least two digital images concurrently. For example, the digital display 790 may display the optimized endoscope digital image 791 and another digital image of the eye 101, such as the optimized digital image of the eye 191, concurrently. The optimized endoscope digital image 791 may be displayed as a main image and another digital image of the eye 101 may be displayed in an inset position. Alternatively, another digital image of the eye 101 may be displayed as the main image and the optimized endoscope digital image 791 may be displayed in an inset position.

The digital display 790 may display the optimized endoscope digital image 791 generated by the processor 780 or another processor and other information generated by the processor 780 or another processor. Such information may include graphic or textual information, such as surgical parameters, surgical modes, flow rates, intraocular pressure, endoscopic video, OCT images, warnings, digital images, color coding or augmented reality information. The processor 780 may reformat video made using the camera 750 for display on the digital display 790, which may be viewed with circularly polarized glasses, digital oculars, or using a head mounted display.

Figure 8:
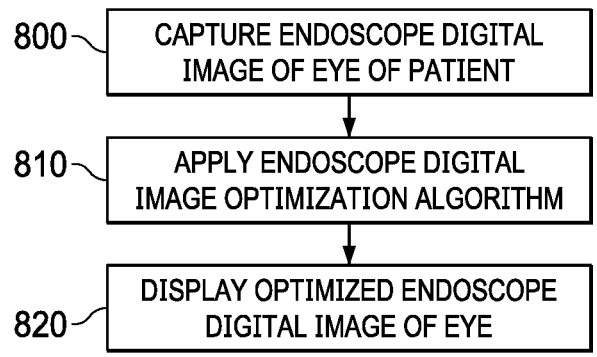
FIG. 8 is a flow diagram illustrating a method of optimizing an endoscope digital image of an eye to improve digital visualization for ophthalmic surgery.

FIG. 8 presents a flow chart for a method of optimizing an endoscope digital image of the eye to improve digital visualization for ophthalmic surgery by using an endoscope digital image optimization algorithm. In step 800, an endoscope digital image of an eye of a patient is captured using an endoscope, such as the endoscope 715. In step 810, an endoscope digital image optimization algorithm is applied to the endoscope digital image of the eye to generate an optimized endoscope digital image of the eye, such as the optimized endoscope digital image of the eye 791. The endoscope digital image optimization algorithm may use interpolation, multi-exposure image noise reduction, machine learning, deep learning, or any combination thereof. In step 820, the optimized endoscope digital image of the eye is displayed on a digital display, such as the digital display 790.

Figure 9:
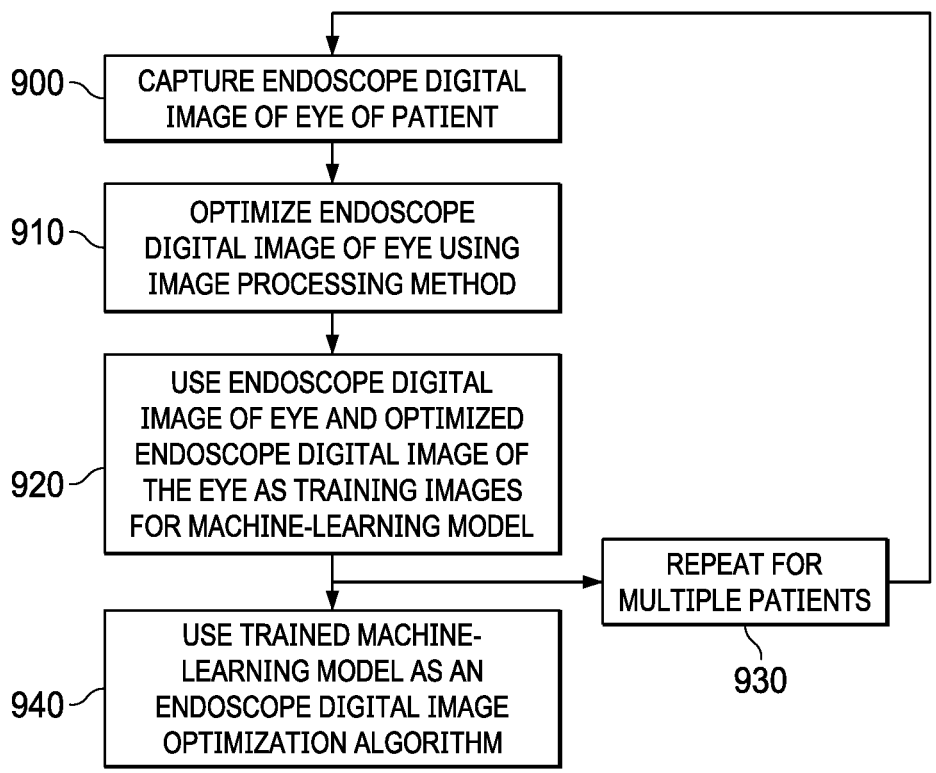
FIG. 9 is a flow diagram illustrating a method of generating an endoscope digital image optimization algorithm using a machine-learning model to improve digital visualization for ophthalmic surgery.

FIG. 9 presents a flow chart for a method of generating an endoscope digital image optimization algorithm using a machine-learning model to improve digital visualization for ophthalmic surgery. In step 900, an endoscope digital image of an eye of a patient is captured, such as an endoscope digital image of the eye 101 captured by the endoscope 715. In step 910, the endoscope digital image of the eye is optimized using an imaging processing method such as interpolation, multi-exposure image noise reduction, or a combination thereof, to generate an optimized endoscope digital image of the eye, such as the optimized endoscope digital image of the eye 791. Optimization of an of endoscope digital image of the eye may be deemed successful if the surgeon successfully completed surgery using the optimized endoscope digital image of the eye. In step 920, the endoscope digital image of the eye and the optimized endoscope digital image of the eye are used as an input image and an output image respectively, in a set of training images to train a machine learning model. In step 930, steps 900-920 are repeated for a plurality of input images and output images of endoscope digital images of multiple patients. These images may be collected from a wide range of surgeons and ophthalmic hospitals. The plurality of input images and output images may be used to train a machine-learning model to predict an output image, for example, an optimized endoscope digital image of the eye, when provided with only an input image, for example, an endoscope digital image of the eye. In step 940, the trained machine-learning model may be used as an endoscope digital image optimization algorithm to improve an endoscope digital image of the eye.

Figure 10:
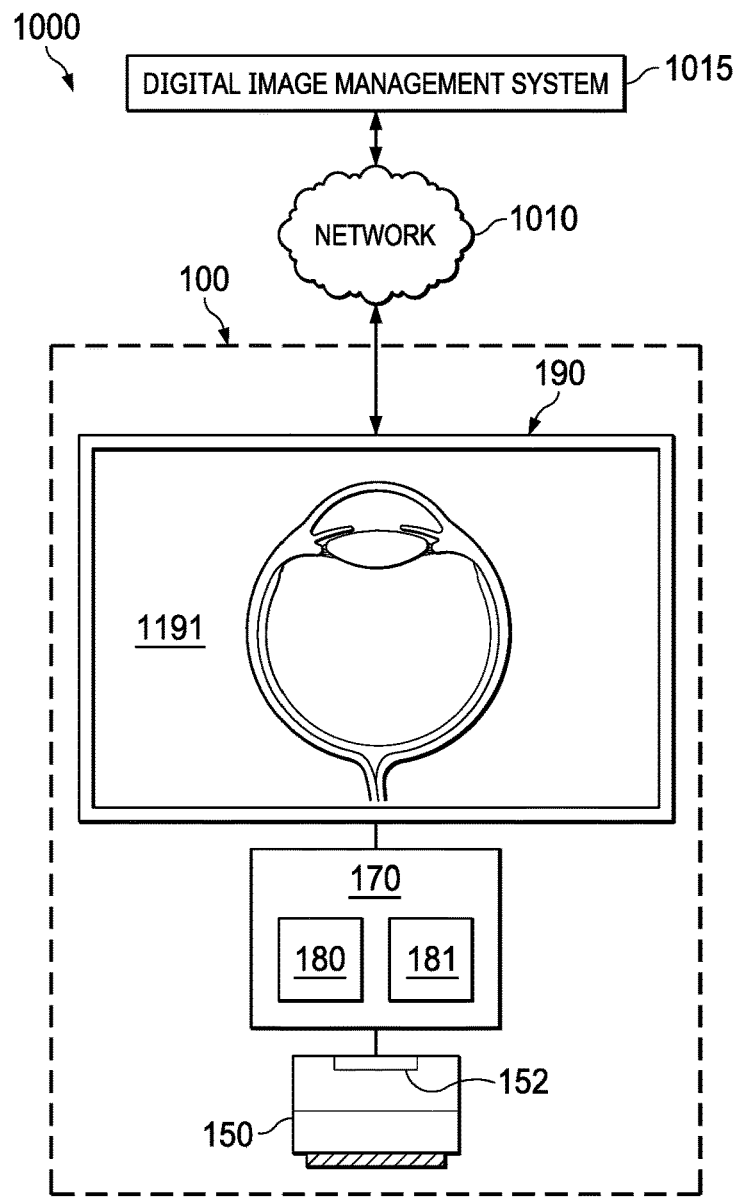
FIG. 10 is a schematic representation of an optimization network including a digital image optimization system, a communication network, and a digital image management system.
Figure 10:
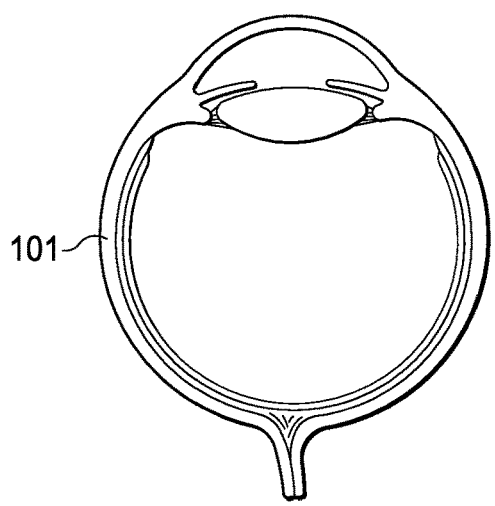

The digital image optimization system 100, the digital image optimization system 500 and the digital image optimization system 700 may be used in conjunction with an optimization network 1000, as depicted in FIG. 10. The optimization network 1000 may further include a communication network 1010 and a digital image management system 1015. FIG. 10 illustrates an example of using the digital image management system 1015 to generate an optimized digital image of the eye 1191 from a digital image of the eye 101. Although FIG. 10 includes the camera 150 in the optimization network 1000, the optimization network 1000 may alternatively include an endoscope, such as the endoscope 715, or any other suitable ophthalmic visualization system. The digital image management system 1015 may communicate with a local image processing system, such as the image processing system 170, over the communication network 1010. Alternatively, the digital image management system 1015 may be part of or include a local image processing system, such as the image processing system 170.

The digital image management system 1015 may use a plurality of training images of the eye 101 to train a machine-learning model. For example, the digital image management system 1015 may use a plurality of digital images of the eye captured at the beginning of a surgery and a plurality of paired digital images of the same eye captured at the conclusion of the surgery, for example, the digital image of the eye at the beginning of surgery 201 and the digital image of the eye at the conclusion of surgery 202, to train a machine-learning model offline. The digital image management system 1015 may alternatively use a plurality of endoscope digital images of the eye that have been successfully optimized using an image processing method to train a machine-learning model offline. The training images used to train the machine-learning model may be uploaded to the digital image management system 1015 via the communication network 1010. The images used to train the machine-learning model may be captured using a Digitally Assisted Vitreoretinal Surgery system, for example an NGENUITY® 3D Visualization System (Novartis AG Corp., Switzerland). The images used to train the machine-learning model may be captured by a plurality of surgeons. The images used to train the machine-learning model may be of a plurality of patients in a plurality of locations. The images used to train the machine-learning model may be of a similar resolution, similar quality, captured with a similar camera, captured during a similar medical procedure, or any combination thereof.

During surgery, the digital image management system 1015 may process a digital image of the eye 101 using the trained machine-learning model to produce an optimized digital image of the eye 1191. The optimized digital image of the eye 1191 may have less instrument glare, less optical aberration, less vitreous fog, or any combination thereof than a digital image of the eye 101 captured by the camera 150 that has not been processed by the digital image management system 1015. The optimized digital image of the eye 1191 may have increased contrast, sharpness, clarity, dynamic range, or any combination thereof than a digital image of the eye 101 captured by the camera 150 that has not been processed by the digital image management system 1015.

Figure 11:
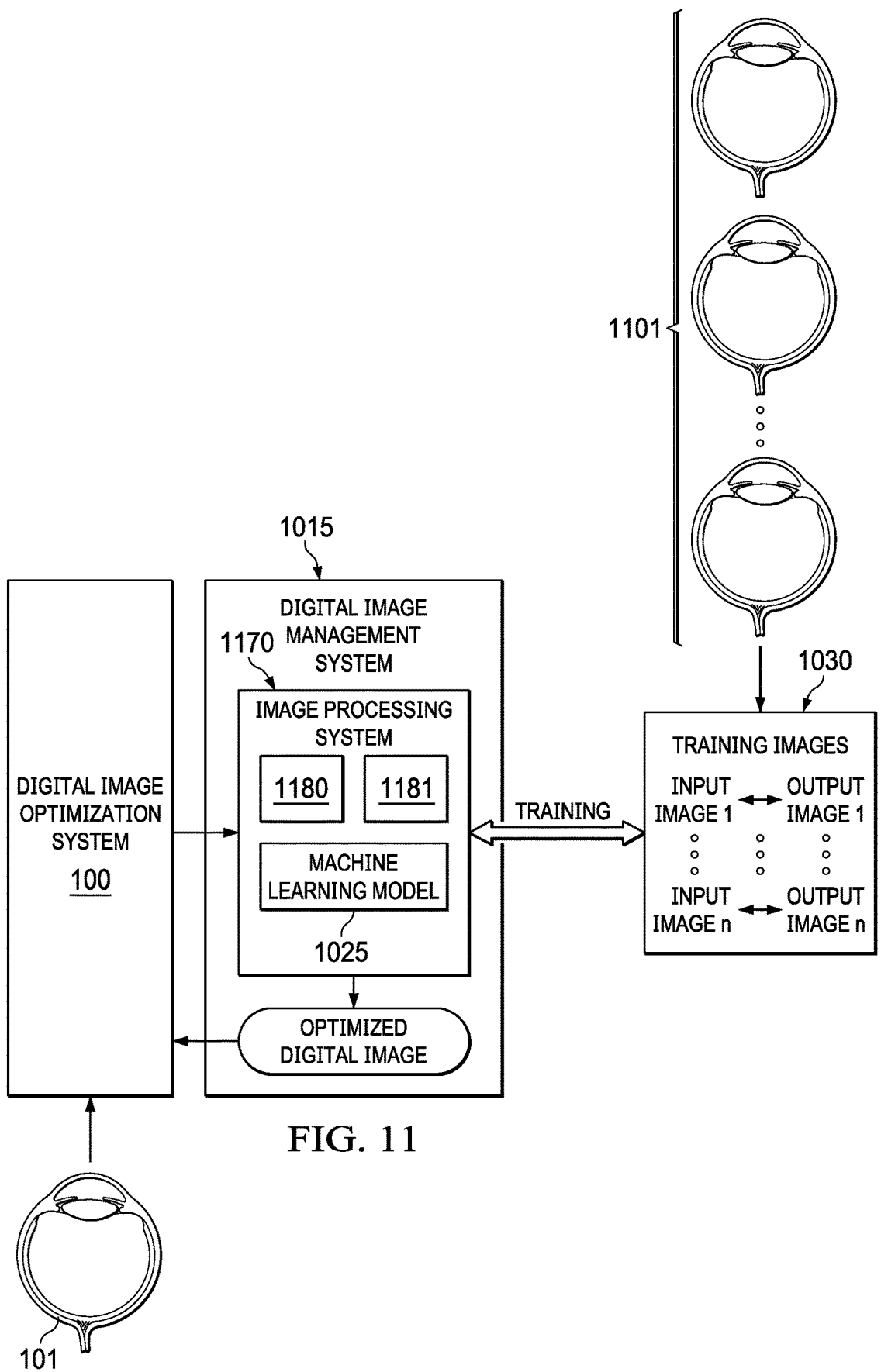
FIG. 11 is an illustration of an example solution for determining an optimized digital image of an eye.

FIG. 11 illustrates an example solution for determining an optimized digital image of the eye, which may be the optimized digital image of the eye 1191. The digital image management system 1015 may include an image processing system 1170, which may further include a processor 1180, a memory medium 1181, and a machine learning model 1025. The image processing system 1170 may determine an optimized digital image of the eye from a digital image of the eye 101 by calculating a differential based on information in the digital image of the eye 101 and combining the differential with the digital image of the eye 101. The differential may be calculated based on the raw pixel data of the digital image of the eye 101. For example, a digital image of the eye 101 may be captured by the digital image optimization system 100 at the beginning of a surgery. The digital image of the eye 101 may include instrument glare, optical aberration, vitreous fog, or any combination thereof. The image processing system 1170 may calculate a differential based on the raw pixel data of the digital image of the eye 101. The differential may be calculated using the machine-learning model 1025. The image processing system 1170 may further determine an optimized digital image of the eye by combining the digital image of the eye 101 with the differential.

As shown in FIG. 11, the digital image optimization system 100 may capture a digital image of the eye 101 and send it to the image processing system 1170. The digital image optimization system 100 may use a communication network, such as the communication network 1010, to send the digital image of the eye 101 to the image processing system 1170. The image processing system 1170 may be included in the digital image management system 1015. The image processing system 1170 may therefore process digital images of an eye that have been captured from remote ophthalmic visualization systems to produce an optimized digital image. Alternatively, the image processing system 1170, once trained, may be stored locally on an ophthalmic visualization system, for example, as the image processing system 170 in the digital image optimization system 100. In this example, the image processing system 1170 may optimize a digital image of the eye 101 locally.

The image processing system 1170 may calculate a differential of a digital image of the eye 101 using the machine-learning model 1025. The machine-learning model 1025 may be trained using a plurality of training images 1030, as depicted in FIG. 11. Training images 1030 may be obtained of a plurality of eyes 1101. Each set of training images 1030 includes an input image, which may be, for example, the digital image of the eye at the beginning of surgery 201, and an output image, which may be, for example, the digital image of the eye at the conclusion of surgery 202. The image processing system 1170 may have access to training images 1030 to train the machine-learning model 1025. The machine-learning model 1025 may be trained based on: (1) extracting features from an input image and (2) learning a relationship function between the extracted features and the differentials between an input image and an output image. The machine-learning model 1025 may therefore be used to predict an output image when provided with only an input image. Alternatively, any suitable training images 1030 may be obtained in any suitable manner to train the machine-learning model 1025 to optimize a digital image of an eye.

Figure 12:
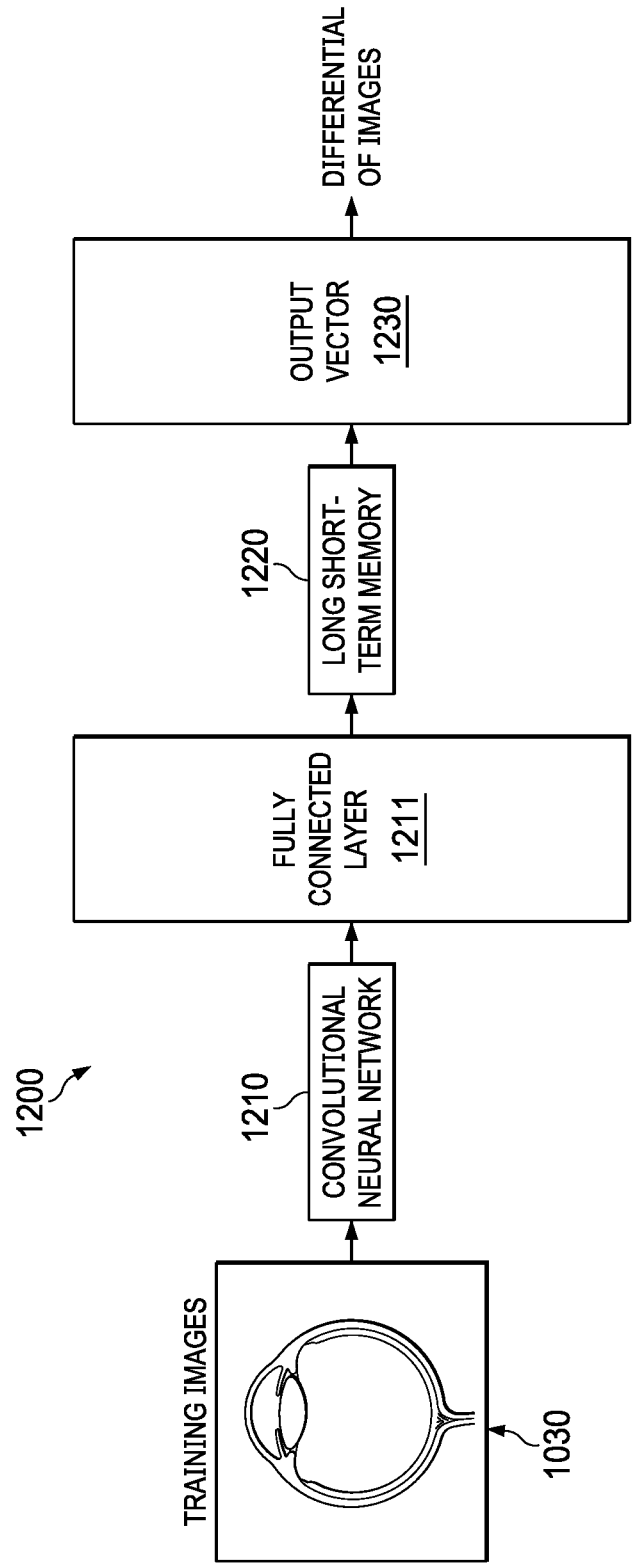
FIG. 12 is an illustration of an example integrated architecture of a machine-learning model.

FIG. 12 illustrates an example integrated architecture 1200 of the machine-learning model 1025 for calculating a differential based on information in the digital image of an eye, for example, for calculating a differential between the digital image of the eye at the beginning of surgery 201 and the digital image of the eye at the conclusion of surgery 202. The integrated architecture 1200 may include a convolutional neural network (CNN) 1210 and at least one long short-term memory unit (LSTM) 1220. The convolutional neural network 1210 may include a class of deep, feed-forward artificial neural networks that may be effective for analyzing images. The convolutional neural network 1210 may use a variation of multi-layer perceptrons designed to require minimal preprocessing. The multi-layer perceptrons may be also known as shift invariant or space invariant artificial neural networks because of their shared-weights architecture and translation invariance characteristics. The convolutional neural network 1210 may include a plurality of sequential layers. The at least one long short-term memory unit 1220 may include a recurrent neural network that may be used as a building component or block of hidden layers for an eventually bigger recurrent neural network. The long short-term memory unit 1220 may itself be a recurrent network because it may contain recurrent connections similar to connections in a conventional recurrent neural network. The convolutional neural network 1210 and the at least one long short-term memory unit 1220 may be integrated. The integration may be achieved by inserting the at least one long short-term memory unit 1220 after the last of the plurality of sequential layers of the convolutional neural network 1210. The convolutional neural network 1210 may include a last sequential layer that is a fully connected layer 1211. The at least one long short-term memory unit 1220 may be inserted after the fully connected layer 1211. The at least one long short-term memory unit 1220 may correspond to raw pixel data of the digital image of the eye, for example image width, image length, color channel data, or any combination thereof. The output of the at least one long short-term memory unit 1220 may be an output vector 1230. The image processing system 1170 may use the output vector 1230 to calculate a differential based on information in the digital image of an eye. As an alternative, the image processing system 1170 may use any suitable architecture to train the machine-learning model 1025.

The image processing system 1170 may generate feature representations for the plurality of training images 1030 by processing the plurality of training images 1030 using the convolutional neural network 1210. The convolutional neural network 1210 may be based on a pre-trained classification network. For example, the pre-trained classification network may include a Residual Network. The image processing system 1170 may implement the convolutional neural network 1210 by modifying the last fully connected layer 1211 of the pre-trained classification network. The image processing system 1170 may use the output of the convolutional neural network 1210 as the generated feature representations of the plurality of training images 1030. An example of a feature representation may be a vector of numeric values. The image processing system 1170 may also use the output of the convolutional neural network 1210 as the input of the at least one long short-term memory unit 1220. As an alternative, feature representations may be generated using any suitable convolutional neural network in any suitable manner.

The image processing system 1170 may learn a relationship function between the feature representations of the plurality of training images 1030 and the differentials between the pairs of input images and output images of the training images 1030. The learning of the relationship function may be based on the machine-learning integrated architecture 1200 and a particular loss function. The relationship function may include a mapping function. The input of the mapping function may include the feature representation of an input image, and a differential between the input image and the corresponding output image. The output of the mapping function may include a differential between a predicted hypothesis optimized digital image of the eye and the corresponding output image. The differential may include a value corresponding to the raw pixel data of the digital image, for example image width, image length, color channel data, or any combination thereof. The mapping function may further be based on a particular loss function. For example, the loss function may be a smooth L1 loss function. For any variable x, the smooth L1 loss function may be defined as:

$$\text{smooth}_{L1}(x) = \begin{cases} 0.5x^2, & \text{if } |x| < 1 \\ |x| - 0.5, & \text{if } |x| \geq 1 \end{cases}$$

As an alternative, the image processing system 1170 may learn any suitable relationship function in any suitable manner.

Figure 13:
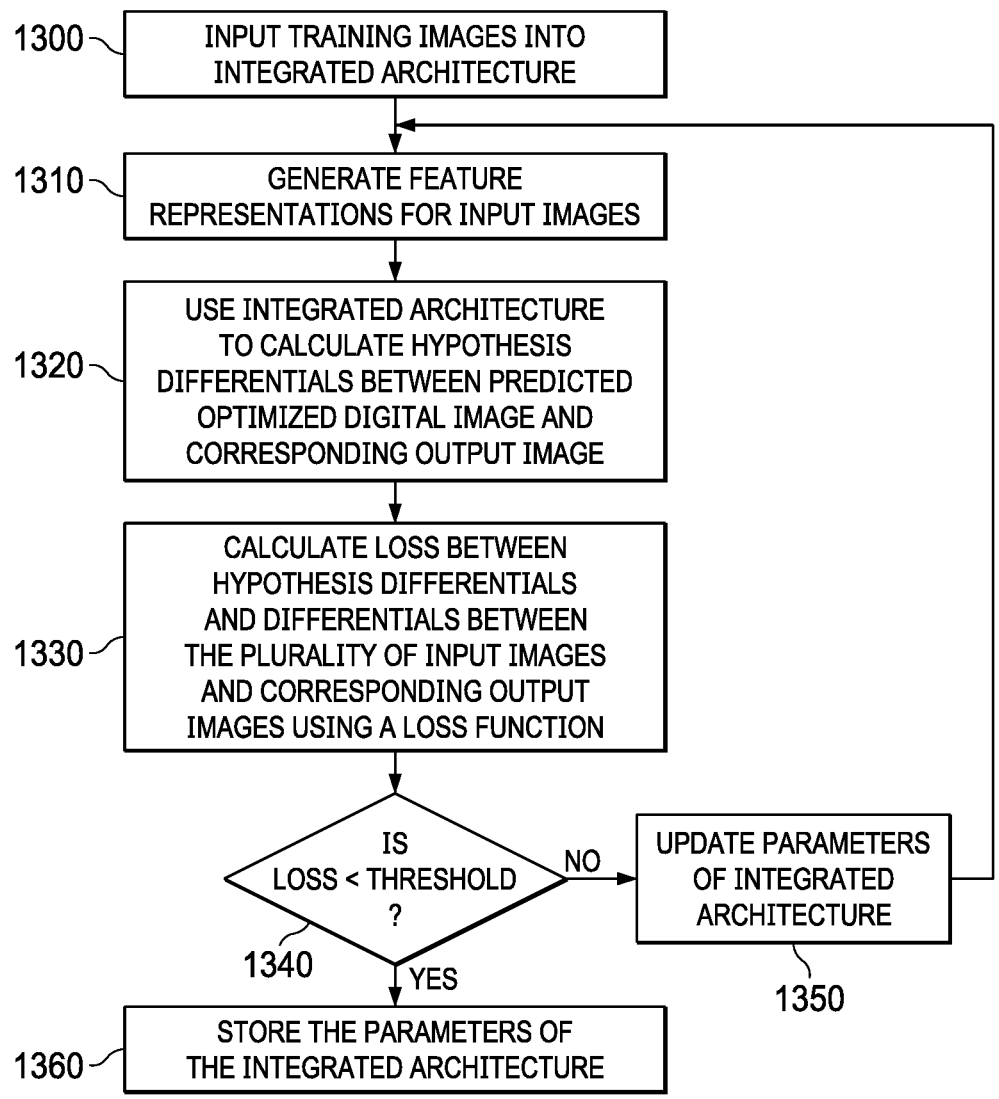
FIG. 13 is a flow diagram illustrating a method of training a machine-learning model.

FIG. 13 presents a flow chart for a method of training a machine-learning model, such as the machine-learning model 1025. In step 1300, an image processing system, such as the image processing system 1170, may input a plurality of training images, such as the training images 1030, into an integrated architecture, such as the integrated architecture 1200. The plurality of training images may include a plurality of input images and a plurality of corresponding output images. An input image may be, for example, the digital image of the eye at the beginning of surgery 201, and an output image may be, for example, the digital image of the eye at the conclusion of surgery 202. In step 1310, the image processing system may use a convolutional neural network, such as the convolutional neural network 1210, to generate feature representations for the plurality of input images of the plurality of training images. In step 1320, the image processing system may use the integrated architecture to calculate a plurality of hypothesis differentials between a plurality of predicted optimized digital images of the eye and their corresponding output images. The plurality of hypothesis differentials may be calculated using the feature representations for the plurality of corresponding input images. In step 1330, the image processing system may calculate a loss between the plurality of hypothesis differentials and a plurality of differentials calculated between the plurality of input images and the plurality of corresponding output images. The loss may be calculated using a loss function, which may include a smooth L1 loss function. In step 1340, the image processing system may evaluate if the overall loss is smaller than a pre-defined threshold value. If the overall loss is not smaller than the pre-defined threshold value, the image processing system may proceed to step 1350. In step 1350, the image processing system may update the parameters of the integrated architecture. The cycle of steps 1310 through 1340 may then be repeated. If the overall loss is smaller than the pre-defined threshold value, the image processing system may proceed to step 1360. In step 1360, the image processing system may store the parameters of the integrated architecture and end the training. This may be because the machine-learning model has converged. Alternatively, any suitable method for the training of a machine-learning model to optimize a digital image of the eye may be used.

The image processing system 1170 may be trained on a system associated with the digital image management system 1015. Once trained, the image processing system 1170 may operate on a server and may be used to provide cloud-based digital image optimization services. Alternatively, once trained, the image processing system 1170 may be distributed to local ophthalmic visualization systems. This may include local digital image optimization systems such as the digital image optimization system 100, the digital image optimization system 500, the digital image optimization system 700, or any combination thereof.

For example, the trained image processing system 1170 may receive a digital image of an eye. The digital image of the eye may be captured by a camera such as the camera 150, or an endoscope, such as the endoscope 715. The image processing system 1170 may calculate an optimized digital image of the eye by processing the digital image of the eye using the trained machine-learning model 1025. The image processing system 1170 may first generate a feature representation for the digital image of the eye by processing the digital image of the eye using the trained machine-learning model 1025, for example, using the convolutional neural network 1210. The image processing system 1170 may then process the generated feature representations and the digital image of the eye using the trained machine-learning model, for example, using at least one long short-term memory unit 1220. The image processing system 1170 may then output a differential between the digital image of the eye and a predicted optimized digital image of the eye. The image processing system 1170 may use this differential to calculate the optimized digital image of the eye from the digital image of the eye. Alternatively, the image processing system 1170 may calculate an optimized digital image of the eye for any digital image of the eye in any suitable manner.

Figure 14:
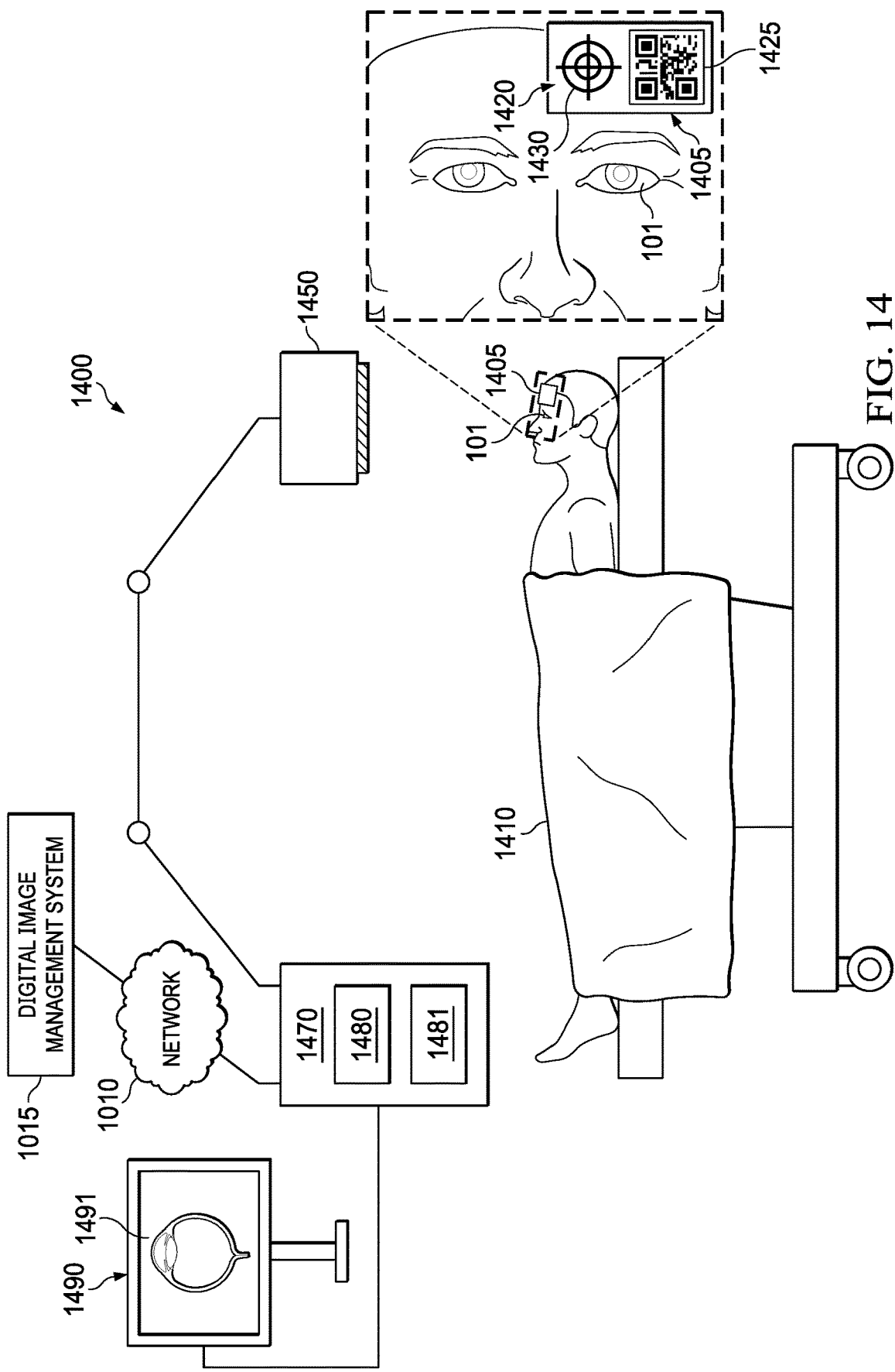
FIG. 14 is a schematic representation of a digital time out system, including an identity marker, a camera, an image processing system, and a digital display.

The digital image optimization system 100, the digital image optimization system 500, the digital image optimization system 700, and the optimization network 1000 may be used in conjunction with a digital time out system 1400, as depicted in FIG. 14. The digital time out system 1400 may include an identity marker 1405, a camera 1450, an image processing system 1470, a digital display 1490, a communication network 1010 and a digital image management system 1015. The image processing system 1470 may further include processor 1480 and memory medium 1481.

The camera 1450 may be a camera such as the camera 150. The camera 1450 may be a component of may be a component of a Digitally Assisted Vitreoretinal Surgery ("DAVS") system, or may be a component of an NGENUITY® 3D Visualization System (Novartis AG Corp., Switzerland). The digital display 1490 may a display such as the digital display 190. The digital display 1490 may be a component of a Digitally Assisted Vitreoretinal Surgery ("DAVS") system, or may be a component of an NGENUITY® 3D Visualization System (Novartis AG Corp., Switzerland).

The identity marker 1405 may be affixed to a patient 1410. The identify marker 1405 may be affixed above the eye 101 of the patient 1410. The identity marker 1405 may be affixed above the eye 101 that is to be operated on of the patient 1410. Alternatively, the identity marker 1405 may be affixed to the patient 1410 in any position that facilitates surgery. The identity marker 1405 may be a removable decal tattoo, a patch, a sticker, tape, or any combination thereof. The identity marker 1405 may also be any other suitable marker to affix to the patient 1410 such that it cannot fall off, cannot smear, cannot be applied incorrectly, or any combination thereof.

The identity marker 1405 may be white on a black background. Alternatively, the identity marker 1405 may be black on a white background. The identity marker 1405 may also include a locator 1430, which may be, for example, a cross-hair. The camera 1450 may identify the locator 1430 and position itself at a specific position relative to the locator 1430. The camera 1450 may be a robotic-controlled camera. The camera 1450 may move with six degrees of freedom. The locator 1430 may allow the camera 1450 to automatically place itself above the eye 101 of the patient 1410.

The identity marker 1405 may include machine-readable information 1420 that is associated with the patient 1410. For example, the machine-readable information 1420 may include machine-readable markings such as a barcode. The bar code may be a single dimensional barcode. The bar code may be a multi-dimensional barcode. The barcode may be a Quick Response (QR) code 1425. In another example, the machine-readable information 1420 may be or include symbols. The symbols may be or include letters of a written language (e.g., English, German, French, Chinese, Russian, etc.) that may be processed via an optical character recognition (OCR) process and/or system.

The machine-readable information 1420 may be used to store information associated with the patient 1410. The information associated with the patient 1410 may include identification information associated with the patient 1410. The identification information may include one or more of a name, a date of birth, and a government identification, among others. The information associated with the patient 1410 may also include medical information associated with the patient 1410. The medical information associated with the patient 1410 may include one or more of a medical procedure, a medication list, the doctor of the patient 1410, a portion of the patient 1410 that is a subject of a medical procedure, one or more drug allergies, a diagnosis, and an orientation of the patient 1410 for a medical procedure, among others. The medical information associated with the patient 1410 may include the eye which is to be operated on, for example, a right eye or a left eye. In another example, the information associated with the patient 1410 may include indexing information. The indexing information may be used to index into a database and/or a storage device that stores information associated with the patient 1410. The indexing information may be used as a key or used to create the key that may be used to retrieve information associated with the patient 1410 from a database and/or a storage device that stores the information associated with the patient 1410.

The machine-readable information 1420 may be printed on the identity marker 1405 on any kind of support media format necessary, for example, paper, cloth, plastic card, sticker, or any combination thereof. The machine-readable information 1420 may include a bar code and/or a custom optical code and/or marking. The camera 1450 may capture a digital image of the identity marker 1405 and send a signal to the processor 1480. The camera 1450 may also capture a digital image of the eye 101 to be operated on of the patient 1410 and send a signal to the processor 1480. The camera 1450 may acquire the machine-readable information 1420. The machine-readable information 1420 may be processed by the image processing system 1470 using the processor 1480. The digital image of the eye 101 of the patient 1410 may also be processed by the image processing system 1470 using the processor 1480. The camera 1450 may acquire the machine-readable information 1420 automatically by recognizing the identity marker 1405 in the operating room. The machine-readable information 1420 may initiate an automatic white balance color calibration of the camera 1450 upon the camera 1450 acquiring the machine-readable information 1420.

Processing the machine-readable information 1420 may include processing one or more images to determine information stored via the machine-readable information 1420. For example, the one or more images may include one or more barcodes that include information associated with a medical procedure. The one or more barcodes may include information described herein, and processing the machine-readable information 1420 may include retrieving information associated with a medical procedure from the machine-readable information 1420.

The machine-readable information 1420 may be processed using the processor 1480 to determine patient data. In one example, the machine-readable information 1420 may include the patient data. In another example, processing the machine-readable information 1420 to determine patient data may include retrieving one or more portions of the patient data from a storage device. Patient data retrieved from a storage device may include information about the planned medical procedure, image data from previous ophthalmic surgeries or examinations, diagnostic data from previous ophthalmic surgeries or examinations, information about previous eye conditions, or any combination thereof. The retrieved patient data may be displayed on the digital display 1490. The retrieved patient data may be displayed as a picture-in-picture display on the digital display 1490. The machine-readable information 1420 may include encrypted information. For example, processing the machine-readable information 1420 to determine patient data may include decrypting information stored via the machine-readable information 1420 to determine patient data.

The machine-readable information 1420 may be read at the beginning of surgery. The machine-readable information 1420 may be read at the conclusion of surgery. Alternatively, the machine-readable information 1420 may be read at any time necessary during surgery. Reading of the machine-readable information 1420 may initiate a digital time out. The digital time out may provide a computational check that the information associated with the patient 1410 matches the information provided to the surgeon, the staff in the operating room, or a combination thereof. The digital time out may be used to detect any errors in the information provided to the surgeon, the staff in the operating room, or a combination thereof compared to the information associated with the patient 1410. For example, the digital time out may provide a surgical equivalent of a parity check of the identity of the patient, the planned medical procedure, the eye to be operated on, or any combination thereof.

The digital time out may confirm the identity of the patient 1410. During the digital time out, the image processing system 1470 may compare the identity information associated with the patient 1410 stored in the machine-readable information 1420 to the information provided to the surgeon, the staff in the operating room, or a combination thereof. During the digital time out, the image processing system 1470 may use the machine-readable information 1420 to retrieve an image of the eye of the patient and compare this image to a digital image of the eye 101 of the patient 1410 captured with the camera 1450. This may confirm the identity of the patient 1410.

The digital time out may confirm the planned medical procedure for the patient 1410. During the digital time out, the image processing system 1470 may compare the identity of the eye to be operated on provided in the medical information associated with the patient 1410 to the identity of the eye to be operated on in the information provided to the surgeon, the staff in the operating room, or a combination thereof. During the digital time out, the image processing system 1470 may compare the medical procedure about to be carried out to the planned medical procedure recorded in the medical information associated with the patient 1410.

The image processing system 1470 may determine discrepancies between the information associated with the patient 1410 provided by the machine-readable information 1420 and the information provided to the surgeon, the staff in the operating room, or a combination thereof. The image processing system 1470 may determine agreement between the information associated with the patient 1410 and the information provided to the surgeon, the staff in the operating room, or a combination thereof. The image processing system 1470 may determine discrepancies, agreement, or a combination thereof, between the information associated with the patient 1410 and the information provided to the surgeon, the staff in the operating room, or a combination thereof, by displaying them on the digital display 1490. Alternatively, the image processing system 1470 may report discrepancies, agreement, or a combination thereof between the information associated with the patient 1410 and the information provided to the surgeon, the staff in the operating room, or a combination thereof, using any suitable means. If discrepancies exist between the information associated with the patient 1410 and the information provided to the surgeon, the staff in the operating room, or a combination thereof, the digital time out system 1400 may prevent the surgeon from using medical equipment, for example, the camera 1450.

The machine-readable information 1420 may also be utilized in an optimization network, for example the optimization network 1000. The machine-readable information 1420 may include indexing information that may be associated with, or digitally stored with, a corresponding patient digital image of the eye 101. For example, indexing information provided by the machine-readable information 1420 may be digitally stored with a corresponding digital image of the eye 101 of the patient 1410 in the digital image management system 1015. The digital image management system 1015 may produce an optimized digital image of the eye 1491 from the digital image of the eye 101. The digital image management system 1015 may communicate with a local image processing system, such as the image processing system 1470, over the communication network 1010.

The digital image management system 1015 may include an image processing system, such as image processing system 1170, that may use the patient digital image of the eye 101 in a set of training images, such as training images 1030, to train a machine-learning model, such as the machine-learning model 1025. Information associated with the patient 1410 provided by the machine-readable information 1420 may provide additional information about the patient digital image of the eye 101. This may be useful in record keeping for storing digital images of the eye in an optimization network. Information associated with the patient 1410 provided by the machine-readable information 1420 may provide additional information about the patient digital image of the eye 101 that may also be useful in selecting training images to train a machine-learning model. For example, information such as gender, age, eye condition, or any combination thereof, may be used to filter digital images of the eye selected as training images to provide a tailored image processing system to calculate an optimized image of the eye 1491.

Figure 15:
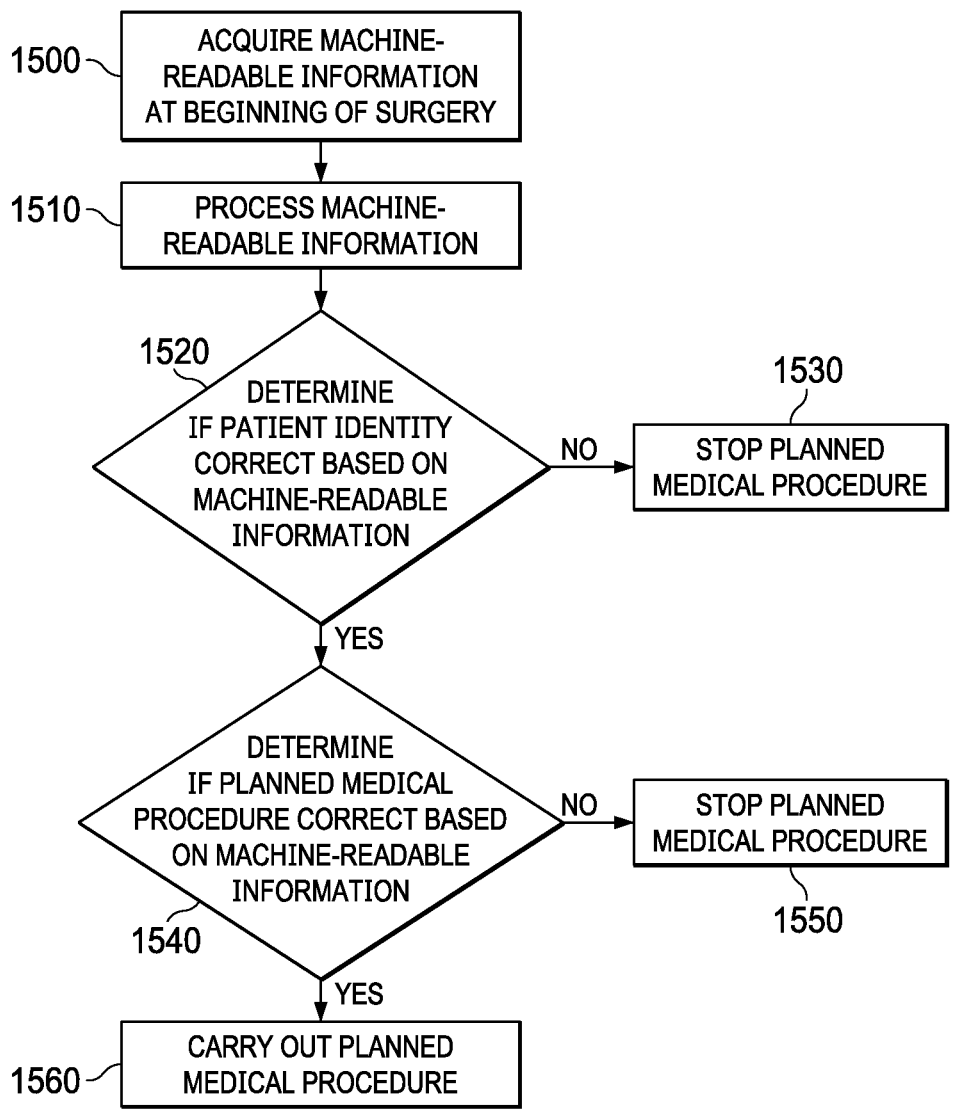
FIG. 15 is a flow diagram illustrating a method of carrying out a digital time out.

FIG. 15 presents a flow chart for a method of carrying out a digital time out. In step 1500, machine-readable information, such as the machine-readable information 1420 printed on the identity marker 1405, may be acquired by a camera, such as the camera 1450. In step 1510, the machine-readable information is processed, for example by the image processing system 1470. In step 1520, the correctness of the patient's identity compared to the information provided to the surgeon, the staff in the operating room, or a combination thereof, is determined based on the machine-readable information. The correctness of the patient's identity may be determined by comparing the identity information associated with patient, such as the identity information associated with the patient 1410, with the information provided to the surgeon, the staff in the operating room, or a combination thereof, which may be, for example, a list of patients scheduled for medical procedures that day. In step 1530, if the identity of the patient is incorrect, the planned medical procedure is stopped. In step 1540, if the identity of the patient is correct, the correctness of the planned medical procedure compared to the information provided to the surgeon, the staff in the operating room, or a combination thereof, is determined based on the machine-readable information. The correctness of the planned medical procedure may be determined by comparing the medical information associated with patient, such as the medical information associated with the patient 1410, with the information provided to the surgeon, the staff in the operating room, or a combination thereof, which may be, for example, a list of planned medical procedures for that day. In step 1550, if the planned medical procedure is incorrect, the planned medical procedure is stopped. In step 1560, if the planned medical procedure is correct, the planned medical procedure is carried out.

Figure 16:
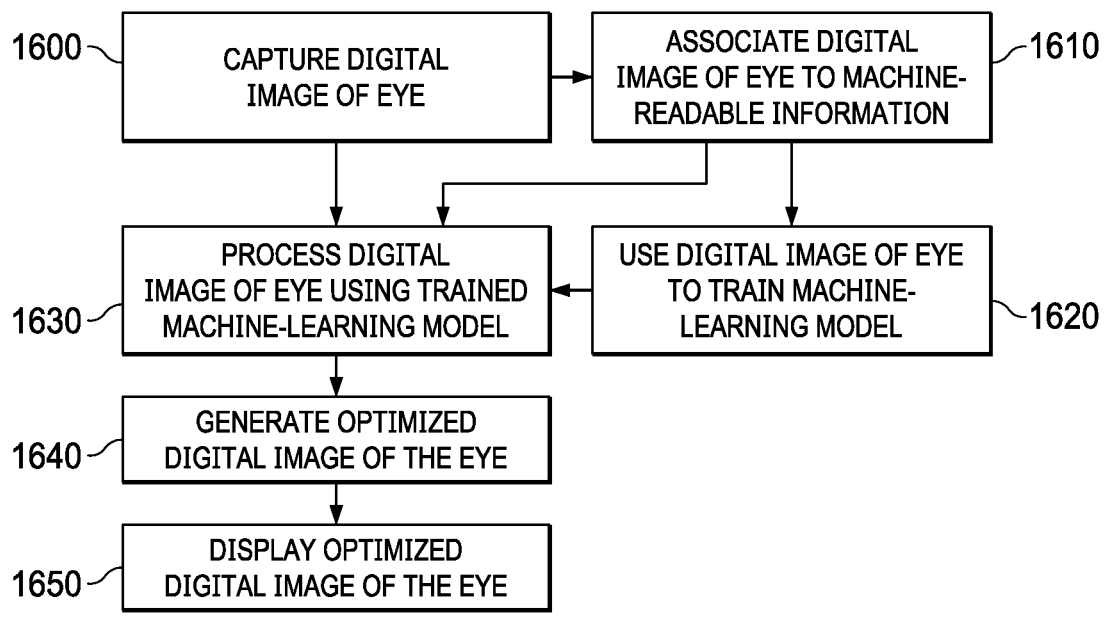
FIG. 16 is a flow diagram illustrating a method of optimizing a digital image of an eye for ophthalmic surgery.

FIG. 16 presents a flow chart for a method of optimizing a digital image of an eye for ophthalmic surgery. In step 1600, a digital image of an eye, such as a digital image of the eye 101, is captured by a digital image optimization system. The digital image optimization system may be, for example, the digital image optimization system 100, and the digital image of the eye may be captured, for example, by the camera 150. In another example, the digital image optimization system may be digital image optimization system 500 and the digital image of the eye may be captured by the camera 550. Alternatively, the digital image optimization system may be digital image optimization system 700 and the digital image of the eye may be captured by an endoscope, such as the endoscope 715. In step 1610, the digital image of the eye is associated with processed machine-readable information, such as the machine-readable information 1420. The machine-readable information may have been processed when the digital image of the eye was captured during a digital time out, for example a digital time out initiated using the digital time out system 1400. The machine-readable information may contain information associated with the patient whose eye is in the digital image of the eye. In step 1620, the digital image of the eye is used to train a machine-learning model, such as the machine-learning model 1025 in the optimization network 1000. For example, the digital image of the eye may be included as an input for a plurality of training images, such as training images 1030. The digital image of the eye may have been selected for inclusion in training images 1030 based on the processed machine-readable information. In step 1630, the digital image of the eye is processed by a trained machine-learning model, such as the trained machine-learning model 1025. In alternative examples, step 1630 may directly follow from step 1600 or step 1610 if the machine-learning model is already trained. In step 1640, an optimized digital image of the eye is produced by an image processing system, for example, the image processing system 1170. In step 1650, the optimized digital image of the eye is displayed on a digital display. For example, the optimized digital image may be displayed on the digital display 190, the digital display 590, the digital display 790, or the digital display 1490.

The digital image optimization system 100, the digital image optimization system 500, the digital image optimization system 700, the optimization network 1000, or the digital time out system 1400 may be used in combination with a computer system 1700, as depicted in FIG. 1700. The computer system 1700 may include a processor 1710, a volatile memory medium 1720, a non-volatile memory medium 1730, and an input/output (I/O) device 1740. The volatile memory medium 1720, the non-volatile memory medium 1730, and the I/O device 1740 may be communicatively coupled to the processor 1710.

Figure 17:
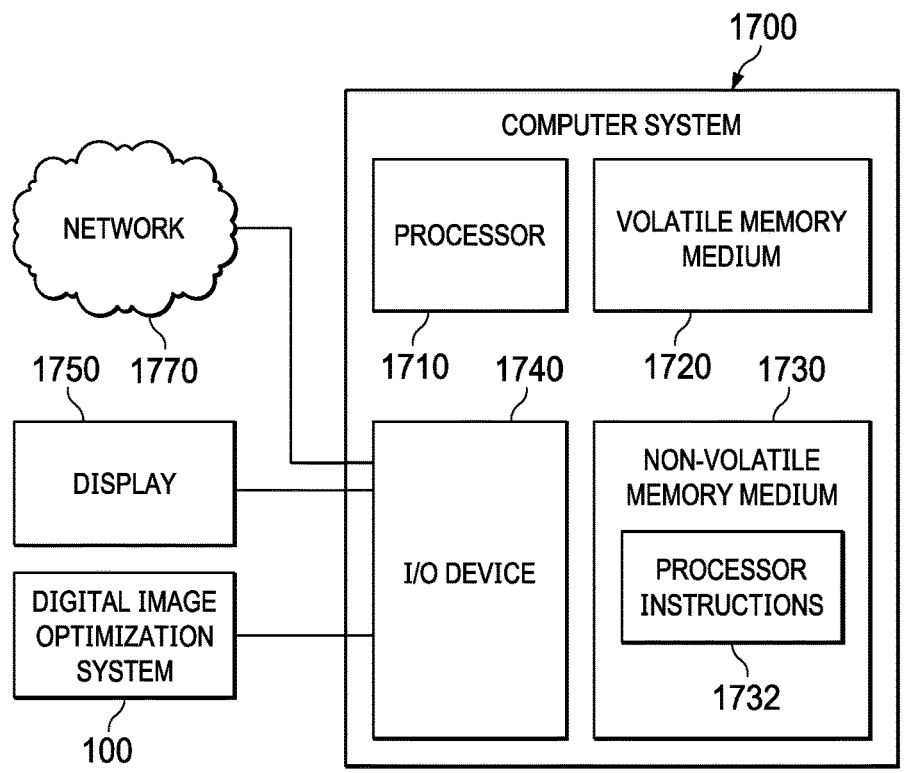
FIG. 17 is a schematic representation of a computer system, including a digital image optimization system.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, or any combination thereof. As shown in FIG. 17, the non-volatile memory medium 1730 may include the processor instructions 1732. The processor instructions 1732 may be executed by the processor 1710. In one example, one or more portions of the processor instructions 1732 may be executed via the non-volatile memory medium 1730. In another example, one or more portions of the processor instructions 1732 may be executed via the volatile memory medium 1720. One or more portions of the processor instructions 1732 may be transferred to the volatile memory medium 1720.

The processor 1710 may execute the processor instructions 1732 in implementing at least a portion of one or more systems, one or more flow charts, one or more processes, and/or one or more methods described herein. For example, the processor instructions 1732 may be configured, coded, and/or encoded with instructions in accordance with at least a portion of one or more systems, one or more flowcharts, one or more methods, and/or one or more processes described herein. Although the processor 1710 is illustrated as a single processor, the processor 1710 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

The processor 1710 may include any suitable system, device, or apparatus operable to interpret and execute program instructions, process data, or both stored in a memory medium and/or received via a network. The processor 1710 further may include one or more microprocessors, microcontrollers, digital signal processors (DSPs), application specific integrated circuits (ASICs), or other circuitry configured to interpret and execute program instructions, process data, or both.

The I/O device 1740 may include any instrumentality or instrumentalities, which allow, permit, and/or enable a user to interact with the computer system 1700 and its associated components by facilitating input from a user and output to a user. Facilitating input from a user may allow the user to manipulate and/or control the computer system 1700, and facilitating output to a user may allow the computer system 1700 to indicate effects of the user's manipulation and/or control. For example, the I/O device 1740 may allow a user to input data, instructions, or both into the computer system 1700, and otherwise manipulate and/or control the computer system 1700 and its associated components. I/O devices may include user interface devices, such as a keyboard, a mouse, a touch screen, a joystick, a handheld lens, a tool tracking device, a coordinate input device, or any other I/O device suitable to be used with a system.

The I/O device 1740 may include one or more buses, one or more serial devices, and/or one or more network interfaces, among others, that may facilitate and/or permit the processor 1710 to implement at least a portion of one or more systems, processes, and/or methods described herein. In one example, the I/O device 1740 may include a storage interface that may facilitate and/or permit the processor 1710 to communicate with an external storage. The storage interface may include one or more of a universal serial bus (USB) interface, a SATA (Serial ATA) interface, a PATA (Parallel ATA) interface, and a small computer system interface (SCSI), among others. In a second example, the I/O device 1740 may include a network interface that may facilitate and/or permit the processor 1710 to communicate with a network. I/O device 1740 may include one or more of a wireless network interface and a wired network interface. In a third example, the I/O device 1740 may include one or more of a peripheral component interconnect (PCI) interface, a PCI Express (PCIe) interface, a serial peripheral interconnect (SPI) interface, and an inter-integrated circuit (I2C) interface, among others. In a fourth example, the I/O device 1740 may include circuitry that may permit the processor 1710 to communicate data with one or more sensors. In a fifth example, the I/O device 1740 may facilitate and/or permit the processor 1710 to communicate data with one or more of a display 1750 and the digital image optimization system 100, among others. As shown in FIG. 17, the I/O device 1740 may be coupled to a network 1770. For example, the I/O device 1740 may include a network interface. In another example, the network 1770 may be or include the network 1010.

The network 1770 may include a wired network, a wireless network, an optical network, or any combination thereof. The network 1770 may include and/or be coupled to various types of communications networks. For example, the network 1770 may include and/or be coupled to a local area network (LAN), a wide area network (WAN), an Internet, a public switched telephone network (PSTN), a cellular telephone network, a satellite telephone network, or any combination thereof. A WAN may include a private WAN, a corporate WAN, a public WAN, or any combination thereof.

Although FIG. 17 illustrates the computer system 1700 as external to the digital image optimization system 100, the digital image optimization system 100 may include the computer system 1700. For example, the processor 1710 may be or include the processor 180.

Figure 18:
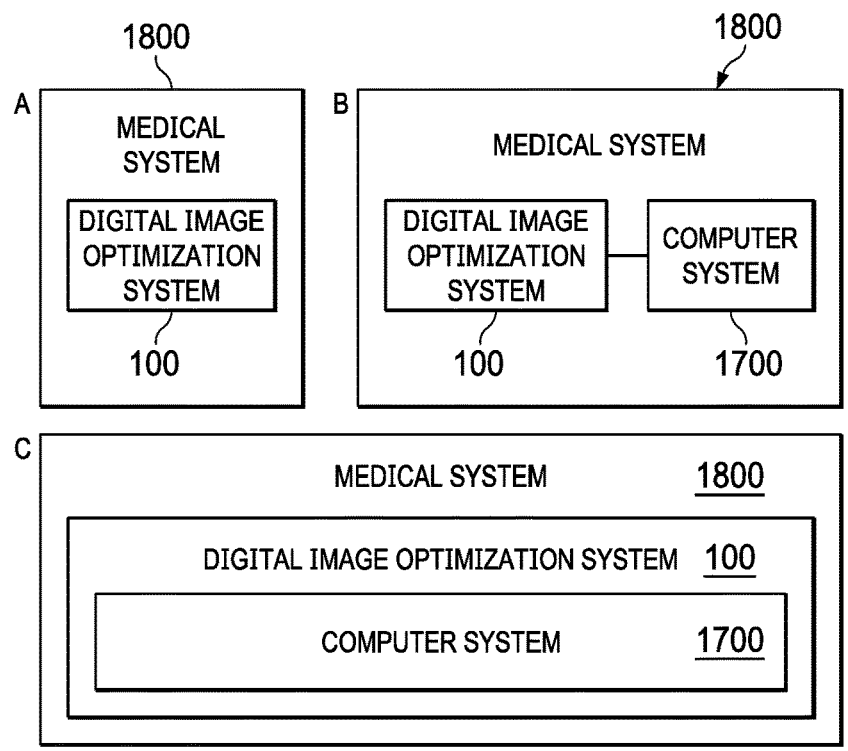
FIGS. 18A-18C are schematic representations of a medical system, including a digital image optimization system.

FIGS. 18A-18C illustrate examples of a medical system 1800. As shown in FIG. 18A, the medical system 1800 may include the digital image optimization system 100. Alternatively, the medical system 1800 may include the digital image optimization system 500, the digital image optimization system 700, the optimization network 1000, the digital time out system 1400, or any combination thereof. As illustrated in FIG. 18B, the medical system 1800 may include the digital image optimization system 100 and the computer system 1700. The digital image optimization system 100 may be communicatively coupled with the computer system 1700. As shown in FIG. 18C, the medical system 1800 may include the digital image optimization system 100, which may include the computer system 1700.

The digital image optimization system 100, the digital image optimization system 500, the digital image optimization system 700, the optimization network 1000, the digital time out system 1400, the computer system 1700, the medical system 1800 and components thereof may be combined with other elements of visualization tools and systems described herein unless clearly mutually exclusive. For instance, the digital image optimization system 500 may be combined with the digital time out system 1400, and may be used with other optimization systems, visualization systems, computer systems, and medical systems described herein.

The above disclosed subject matter is to be considered illustrative, and not restrictive, and the appended claims are intended to cover all such modifications, enhancements, and other embodiments which fall within the true spirit and scope of the present disclosure. For example, although a digital image optimization system is most commonly needed to improve digital visualization for ophthalmic surgery, if it were useful in another procedure, such as a purely diagnostic procedure not otherwise considered to be surgery, the systems and methods described herein may be employed.

The invention claimed is:

1. A digital image optimization system comprising:
a camera comprising at least one sensor operable to detect light reflected off an eye and send a signal corresponding to the detected light to a processor;
an image processing system comprising the processor and operable to:
execute instructions to produce a digital image of the eye; and
execute instructions to apply a digital image optimization algorithm comprising a trained machine-learning model to the digital image of the eye to generate an optimized digital image of the eye, wherein the digital image optimization algorithm at least partially reduces instrument glare, optical aberration, vitreous fog, or any combination thereof, in the digital image of the eye to generate the optimized digital image of the eye, wherein the trained machine-learning model is trained based on a plurality of training images comprising (i) a plurality of input images of eyes of a plurality of patients before or during surgery and (ii) a plurality of output images of the eyes of the plurality of patients at a conclusion of or after surgery, the plurality of output images having a reduction in at least one of instrument glare, optical aberration, or vitreous fog relative to the plurality of input images, and the trained machine-learning model being trained to predict an output image of an eye of each patient included in the plurality of patients at a conclusion of or after surgery based on being provided with an input image of an eye of each patient included in the plurality of patients before or during surgery; and a digital display operable to display the optimized digital image of the eye.

2. The digital image optimization system of claim 1 wherein the optimized digital image of the eye has contrast, sharpness, clarity, dynamic range, or any combination thereof that is the same or increased than that of the digital image of the eye.

3. The digital image optimization system of claim 1, wherein the optimized digital image of the eye has noise, distortion, vignetting, or any combination thereof that is the same or decreased than that of the digital image of the eye.

4. The digital image optimization system of claim 1 wherein the digital image optimization algorithm utilizes interpolation, multi-exposure image noise reduction, or a combination thereof to generate the optimized digital image of the eye.

5. The digital image optimization system of claim 1 wherein the plurality of training images is obtained from a red boost library.

6. The digital image optimization system of claim 1, wherein the trained machine-learning model is trained by (i) extracting features from the input image of the eye before or during surgery and (ii) learning a relationship function between the extracted features and differentials between the input image and the output image of the eye at a conclusion of or after surgery.

7. A digital image optimization system comprising:
an endoscope comprising an optical fiber;
a camera comprising at least one sensor operable to detect light reflected off an interior of an eye and propagated through the optical fiber and send a signal corresponding to the detected light to a processor;
an image processing system comprising the processor and operable to:
execute instructions to produce an endoscope digital image of the eye; and
execute instructions to apply an endoscope digital image optimization algorithm comprising a trained machine-learning model to the endoscope digital image of the eye to generate an optimized endoscope digital image of the eye, wherein the digital image optimization algorithm at least partially reduces instrument glare, optical aberration, vitreous fog, or any combination thereof in the digital image of the eye to generate the optimized digital image of the eye, wherein the trained machine-learning model is trained based on a plurality of training images comprising (i) a plurality of input images of eyes of a plurality of patients before or during surgery and (ii) a plurality of output images of the eyes of the plurality of patients at a conclusion of or after surgery, the plurality of output images having a reduction in at least one of instrument glare, optical aberration, or vitreous fog relative to the plurality of input images, and the trained machine-learning model being trained to predict an output image of an eye at a conclusion of or after surgery based on being provided with an input image of the eye before or during surgery; and a digital display operable to display the optimized endoscope digital image of the eye.

8. The digital image optimization system of claim 7 wherein the endoscope digital image optimization algorithm utilizes interpolation, multi-exposure image noise reduction, or a combination thereof to generate an optimized endoscope digital image of the eye.

9. The digital image optimization system of claim 7 wherein the machine-learning model was trained using a plurality of training images comprising a plurality of endoscope digital images of the eye that were successfully optimized using an image processing method.

10. The digital image optimization system of claim 7 wherein the endoscope digital image optimization algorithm utilizes single image super resolution to generate the optimized endoscope digital image of the eye.

11. The digital image optimization system of claim 10 wherein the single image super resolution uses a very-deep super-resolution neural network.

12. The digital image optimization system of claim 7 wherein the endoscope digital image optimization algorithm at least partially reduces noise, increases resolution, improves digital image quality, or any combination thereof, of the endoscope digital image of the eye.

13. A digital image optimization system comprising:
a camera comprising at least one sensor operable to detect light reflected off an eye and send a signal corresponding to the detected light to a processor;
an image processing system comprising the processor and operable to:
execute instructions to produce a digital image of the eye; and
execute instructions to apply a digital image optimization algorithm comprising a trained machine-learning model to the digital image of the eye to generate an optimized digital image of the eye, wherein the digital image optimization algorithm at least partially reduces instrument glare, optical aberration, vitreous fog, or any combination thereof, in the digital image of the eye to generate the optimized digital image of the eye, wherein the trained machine-learning model is trained based on a plurality of training images comprising (i) a plurality of input images of eyes of a plurality of patients before or during surgery and (ii) a plurality of output images of the eyes of the plurality of patients at a conclusion of or after surgery, the plurality of output images having a reduction in at least one of instrument glare, optical aberration, or vitreous fog relative to the plurality of input images, and the trained machine-learning model being trained to predict an output image of an eye of each patient included in the plurality of patients at a conclusion of or after surgery based on being provided with an input image of an eye of each patient included in the plurality of patients before or during surgery; and a digital display operable to display the optimized digital image of the eye.

* * * * *